US006657169B2

(12) United States Patent
Brown

(10) Patent No.: US 6,657,169 B2

(45) **Date of Patent: *Dec. 2, 2003**

(54) APPARATUS FOR THERMALLY CYCLING SAMPLES OF BIOLOGICAL MATERIAL WITH SUBSTANTIAL TEMPERATURE UNIFORMITY

(75) Inventor: Larry Richard Brown, San Diego, CA (US)

(73) Assignee: Stratagene, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/364,051

(22) Filed: Jul. 30, 1999

(65) Prior Publication Data

US 2002/0030044 A1 Mar. 14, 2002

(51) Int. Cl.[7] ............................ H05B 3/00; C12M 1/00

(52) U.S. Cl. ...................... 219/476; 219/385; 219/521; 219/530; 422/104; 435/285.1; 435/288.4; 62/3.3

(58) Field of Search ........................ 219/476, 477–479, 219/521, 530, 540, 385; 422/99, 104; 135/285.1, 288.4, 303.1; 935/85, 88; 62/3.3

(56) References Cited

U.S. PATENT DOCUMENTS

| | | | | | |
|---|---|---|---|---|---|
| 4,195,131 | A | * | 3/1980 | Papas | 435/286.1 |
| 4,365,665 | A | * | 12/1982 | Nakamura | 165/80.3 |
| 4,865,986 | A | * | 9/1989 | Coy et al. | 435/285.1 |
| 4,950,608 | A | * | 8/1990 | Kishimoto | 422/102 |
| 5,061,630 | A | * | 10/1991 | Knopf et al. | 422/99 |
| 5,255,976 | A | * | 10/1993 | Connelly | 374/31 |
| 5,475,610 | A | | 12/1995 | Atwood et al. | |
| 5,525,300 | A | * | 6/1996 | Danssaert et al. | 935/303.1 |
| 5,602,756 | A | | 2/1997 | Atwood et al. | |
| 5,616,301 | A | * | 4/1997 | Moser et al. | 422/104 |
| 5,710,381 | A | * | 1/1998 | Atwood et al. | 73/864.91 |
| 5,779,981 | A | * | 7/1998 | Danssaert et al. | 62/3.3 |
| 5,785,926 | A | | 7/1998 | Seubert et al. | |
| 5,813,233 | A | | 9/1998 | Okuda et al. | |
| 5,819,842 | A | * | 10/1998 | Potter et al. | 165/206 |
| 5,849,208 | A | * | 12/1998 | Hayes et al. | 216/94 |
| 6,004,512 | A | * | 12/1999 | Titcomb et al. | 422/63 |
| 6,093,370 | A | * | 7/2000 | Yasuda et al. | 422/68.1 |
| 6,106,784 | A | * | 8/2000 | Lund et al. | 422/104 |
| 6,337,435 | B1 | * | 1/2002 | Chu et al. | 136/242 |
| 6,489,111 | B1 | * | 12/2002 | Takahashi et al. | 435/6 |
| 6,558,947 | B1 | * | 5/2003 | Lund et al. | 435/303.1 |
| 2002/0179590 | A1 | * | 12/2002 | Kwasnoski et al. | 219/385 |

FOREIGN PATENT DOCUMENTS

| | | | |
|---|---|---|---|
| EP | 438883 | | 7/1991 |
| EP | 488769 | | 6/1992 |
| JP | 5-168459 | * | 7/1993 |
| JP | 7-308183 | * | 11/1995 |
| JP | 9-322755 | * | 12/1997 |
| WO | 89/12502 | | 12/1989 |
| WO | 9843740 | * | 10/1998 |
| WO | 0032312 | * | 6/2000 |

* cited by examiner

*Primary Examiner*—John A. Jeffery

(74) *Attorney, Agent, or Firm*—Palmer & Dodge LLP; Kathleen M. Williams; David J. Dykeman

(57) ABSTRACT

An apparatus for thermally cycling samples of a biological material including a thermal block assembly including a plurality of sample holders for receiving samples of biological material; a heat sink thermally coupled to the thermal block assembly, the heat sink transferring heat away from the thermal block assembly to ambient air in contact with the heat sink; a first heat source thermally coupled to the thermal block assembly to provide heat to the thermal block assembly; and a second heat source thermally coupled to the first heat source and configured to provide heat to a portion of the first heat source. The arrangement of the heat sink, first heat source and second heat source can provide substantial temperature uniformity among the plurality of sample holders. The invention also includes a method for thermally cycling samples of biological material.

38 Claims, 20 Drawing Sheets

APPARATUS FOR THERMALLY CYCLING SAMPLES OF BIOLOGICAL MATERIAL WITH SUBSTANTIAL TEMPERATURE UNIFORMITY

BACKGROUND OF THE INVENTION

1. Field of the Invention

This invention relates to an apparatus for heating samples of biological material, and more particularly an apparatus for thermal cycling of DNA samples to accomplish a polymerase chain reaction, a quantitative polymerase chain reaction, a reverse transcription-polymerase chain reaction, or other nucleic acid amplification types of experiments.

2. Description of the Related Art

Currently, techniques for thermal cycling of DNA samples are well-known. By performing a polymerase chain reaction (PCR), DNA can be amplified. It is desirable to cycle a specially constituted liquid biological reaction mixture through a specific duration and range of temperatures in order to successfully amplify the DNA in the liquid reaction mixture. Thermocycling is the process of melting DNA, annealing short primers to the resulting single strands, and extending those primers to make new copies of double stranded DNA. The liquid reaction mixture is repeatedly put through this process of melting at high temperatures and annealing and extending at lower temperatures.

In a typical thermocycling apparatus, a biological reaction mixture including DNA will be provided in a large number of sample wells on a thermal block assembly. It is desirable that the samples of DNA have temperatures throughout the thermocycling process that are as uniform as reasonably possible. Even small variations in the temperature between one sample well and another sample well can cause a failure or undesirable outcome of the experiment. For instance, in quantitative PCR, one objective is to perform PCR amplification as precisely as possible by increasing the amount of DNA that generally doubles on every cycle; otherwise there can be an undesirable degree of disparity between the amount of resultant mixtures in the sample wells. If sufficiently uniform temperatures are not obtained by the sample wells, the desired doubling at each cycle may not occur. Although the theoretical doubling of DNA rarely occurs in practice, it is desired that the amplification occurs as efficiently as possible.

In addition, temperature errors can cause the reactions to improperly occur. For example, if the samples are not controlled to have the proper annealing temperatures, certain forms of DNA may not extend properly. This can result in the primers in the mixture annealing to the wrong DNA or not annealing at all. Moreover, by ensuring that all samples are uniformly heated, the dwell times at any temperature can be shortened, thereby speeding up the total PCR cycle time. By shortening this dwell time at certain temperatures, the lifetime and amplification efficiency of the enzyme are increased. Therefore, undesirable temperature errors and variations between the sample well temperatures should be decreased.

In light of the foregoing, there is a need for a thermocycling apparatus that enhances temperature uniformity for the DNA sample wells in the apparatus.

SUMMARY OF THE INVENTION

The advantages and purposes of the invention will be set forth in part in the description which follows, and in part will be apparent from the description, or may be appreciated by practice of the invention. The advantages and purposes of the invention will be realized and attained by means of the elements and combinations particularly pointed out in the appended claims.

To attain the advantages and in accordance with the purposes of the invention, as embodied and broadly described herein, the invention includes an apparatus for heating samples of biological material. The apparatus in its preferred embodiment includes: a thermal block assembly including a plurality of sample holders for receiving samples of biological material; a heat sink thermally coupled to the thermal block assembly, the heat sink transferring heat away from the thermal block assembly to ambient air in contact with the heat sink; a first heat source thermally coupled to the thermal block assembly to provide heat to the thermal block assembly; and a second heat source thermally coupled to the first heat source and configured to provide heat to at least a portion of the first heat source. The arrangement of the heat sink, first heat source and second heat source can provide substantial temperature uniformity among the plurality of sample holders.

In another aspect, the apparatus includes: a thermal block assembly including a plurality of sample wells for receiving samples of biological material; and a first cover of insulating material. The first cover tends to thermally insulate the sample wells of the thermal block assembly. The first cover includes a plate with a plurality of cylindrical sample well openings. Each cylindrical sample well opening corresponds to a respective sample well. The first cover surrounds the top and extends over at least a portion of the sides of the thermal block assembly.

In a further aspect of the invention, the invention includes a method for thermally cycling samples of biological material in an apparatus with at least one sample holder located in a thermal block assembly. The method includes the steps of inserting at least one sample of biological material into a sample holder of the apparatus; measuring the temperature of the thermal block assembly at at least one location on the thermal block assembly; calculating the desired temperature of the thermal block assembly; comparing the desired temperature with the measured temperature, and if the measured temperature is less than the desired temperature, the method further comprises the steps of: applying a first heat source, a portion of the heat from the first heat source being transferred to the thermal block assembly; applying a second heat source, a portion of the heat from the second heat source being transferred to the first heat source; and applying a third heat source, a portion of the heat from the third heat source being transferred to the sample holders; if the measured temperature is greater than the desired temperature, the method further comprises the step of cooling the thermal block assembly by imparting a cooling convection current on a heat sink which is thermally coupled to the thermal block assembly to provide heat transfer from the thermal block assembly to ambient air in contact with the heat sink; and repeating the steps of measuring, calculating, and comparing until the predetermined thermal cycle for the samples of biological material is completed.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

Figure 1:
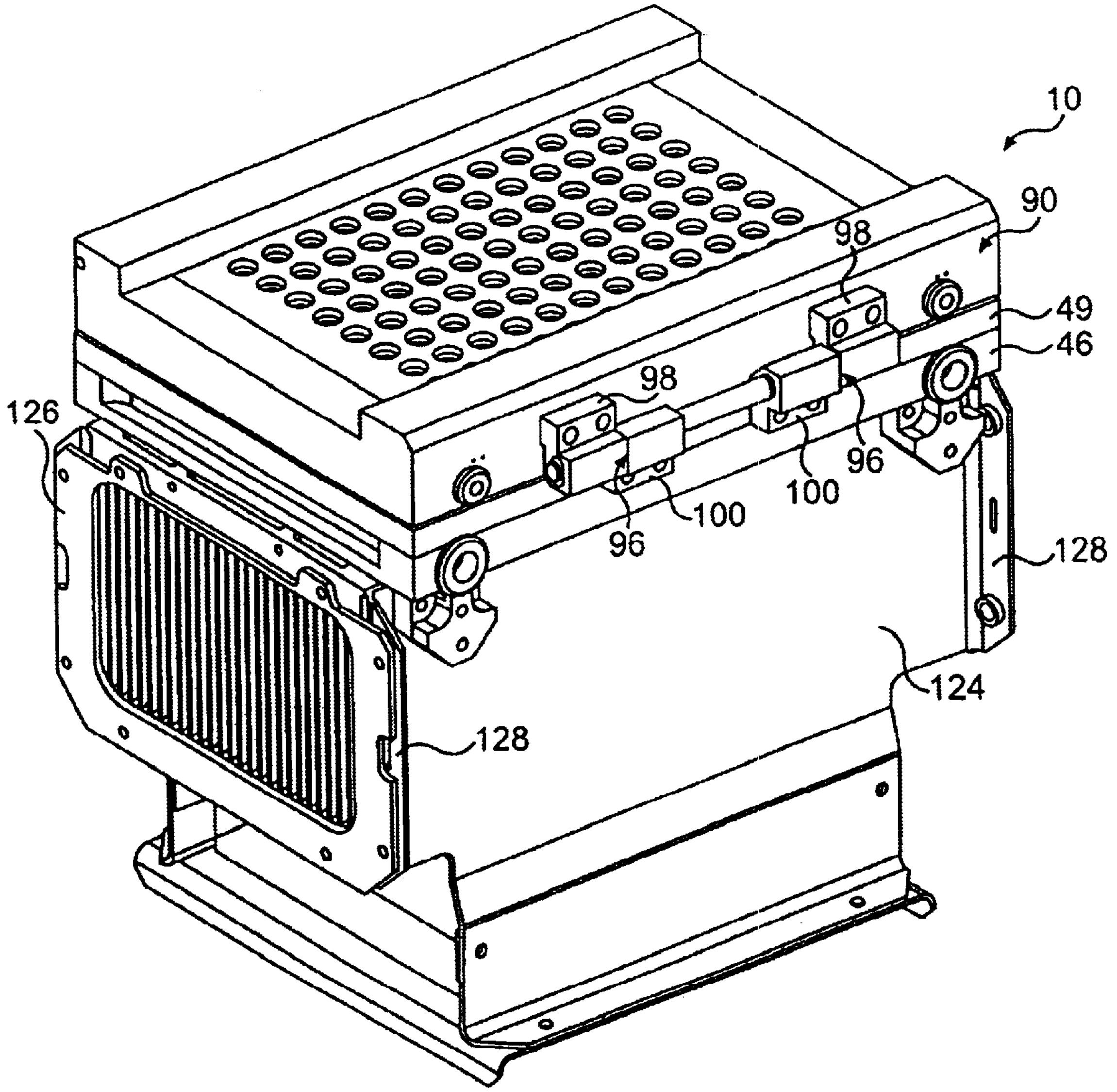
FIG. 1 is a perspective view of the apparatus for thermally cycling samples of a biological material according to the invention.
Figure 2:
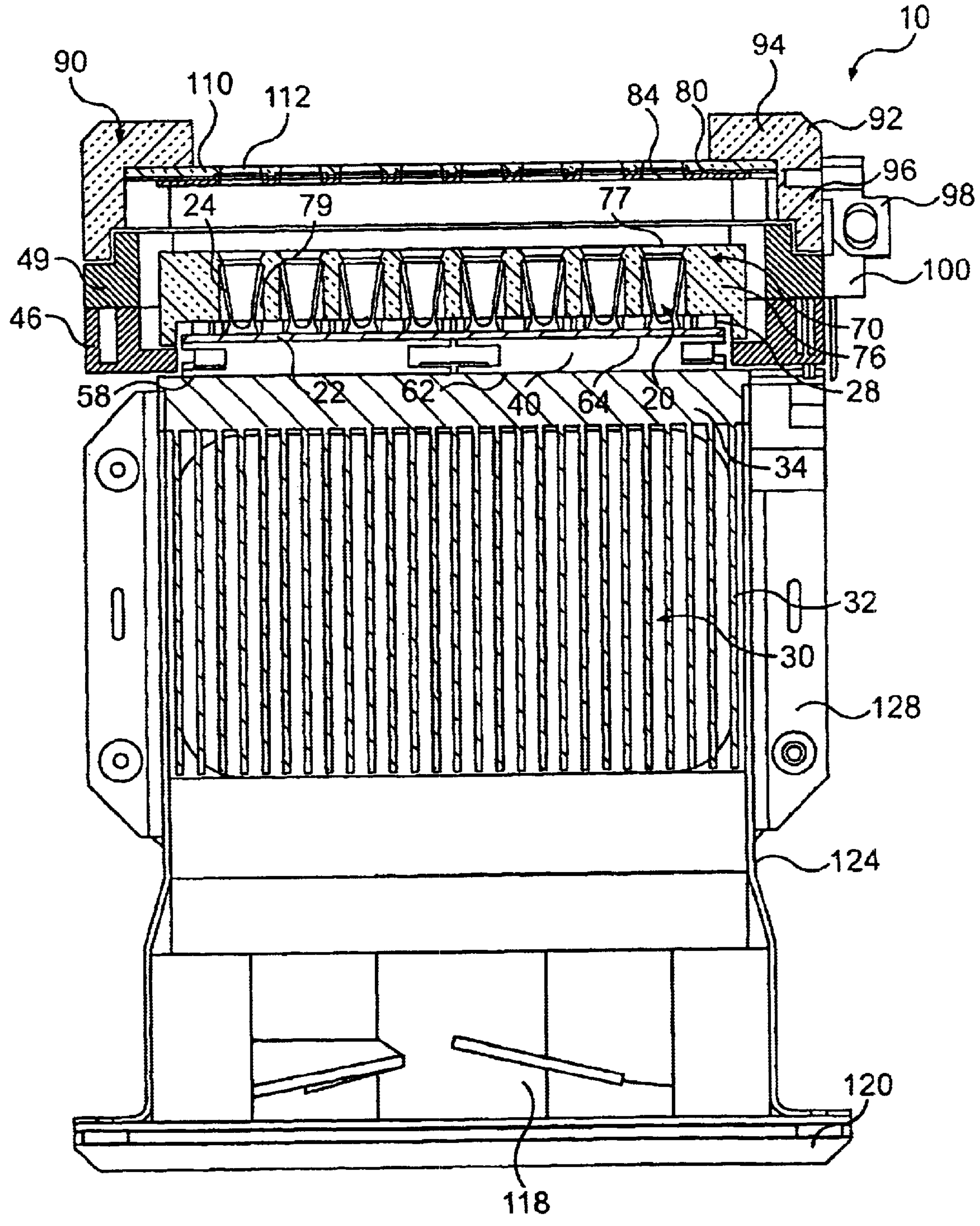
FIG. 2 is a front sectional view of the apparatus of FIG. 1.
Figure 3:
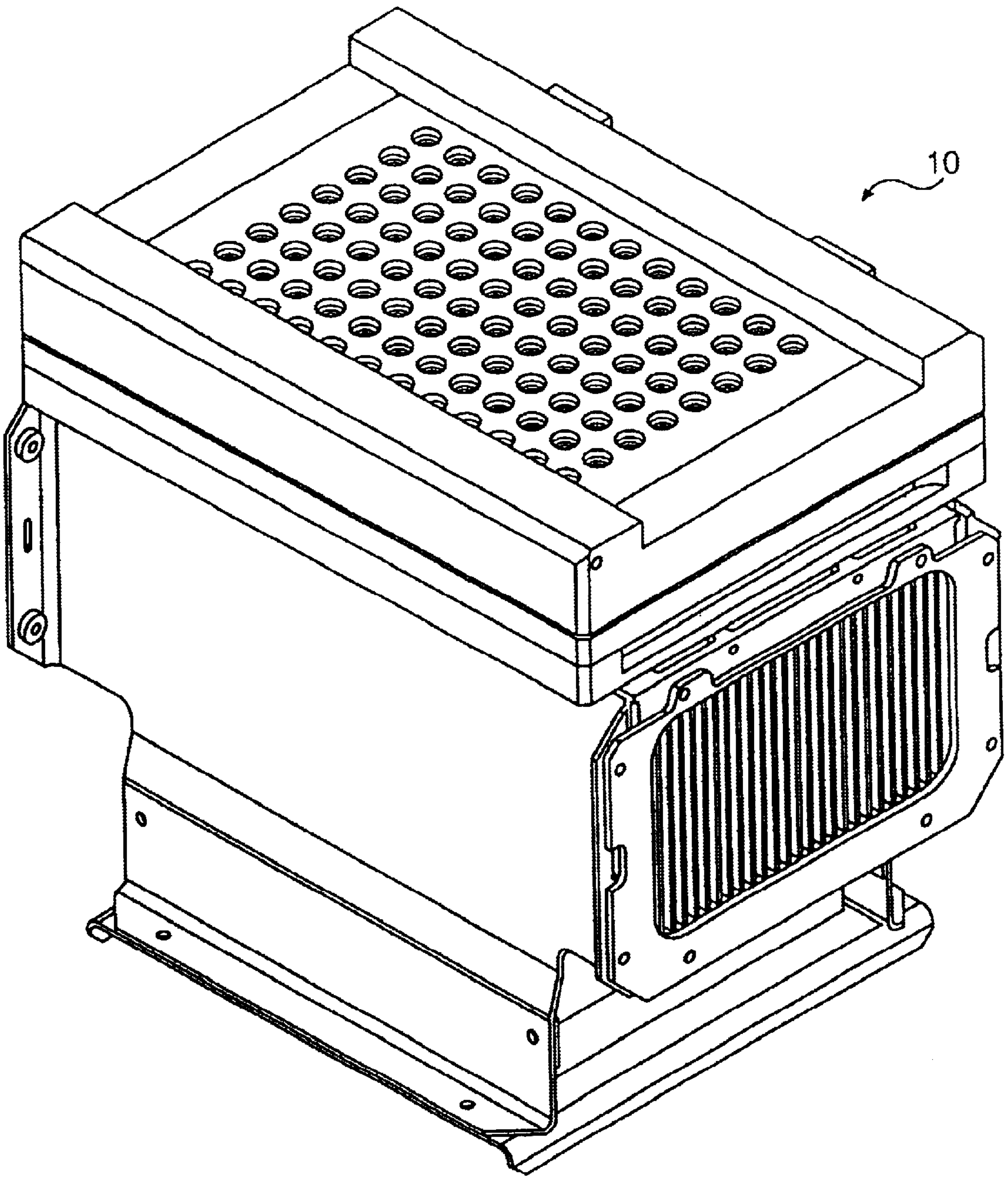
FIG. 3 is another perspective view of the apparatus of FIG. 1.
Figure 4:
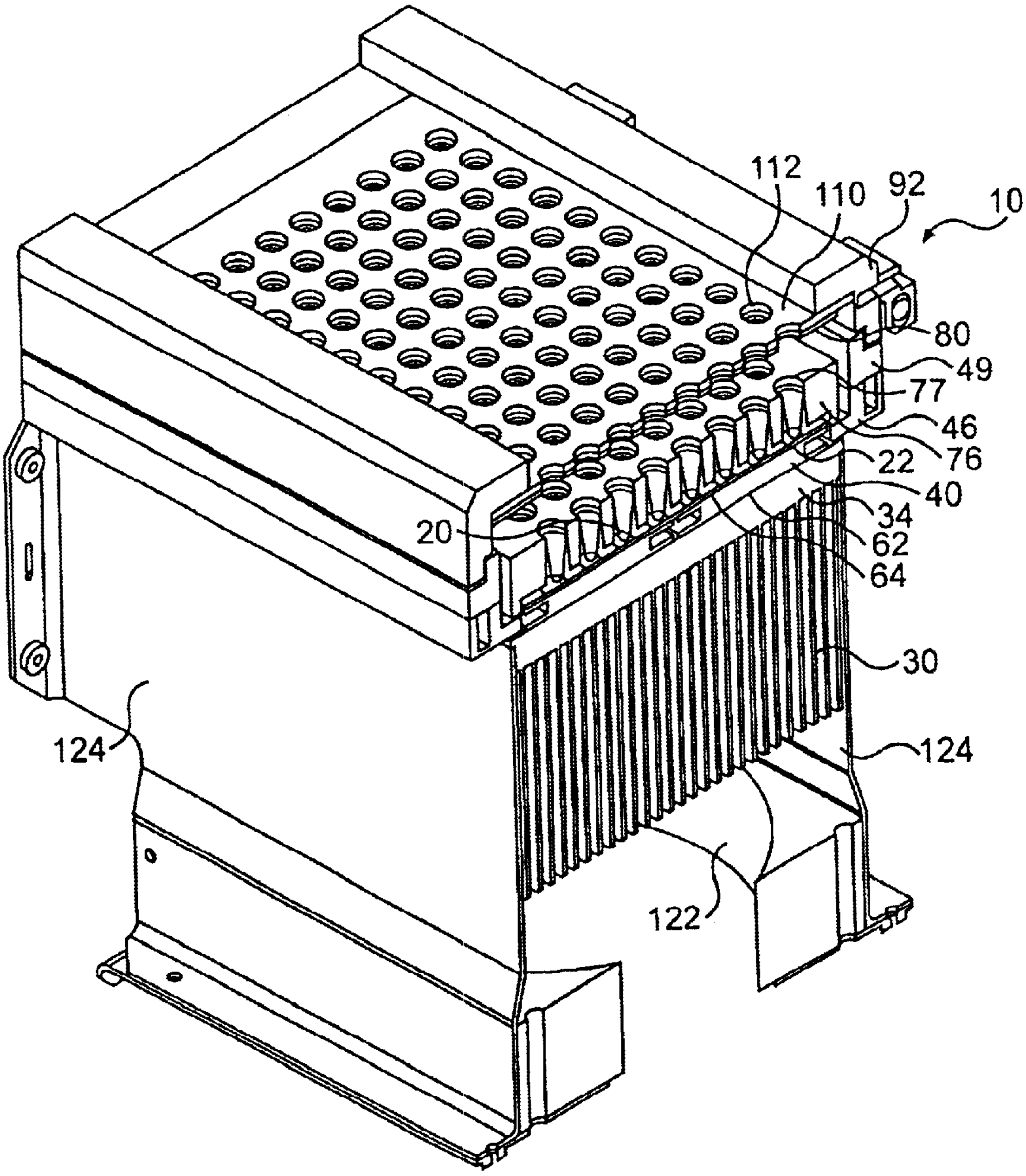
FIG. 4 is a perspective cutaway view of the apparatus of FIG. 1.
Figure 5:
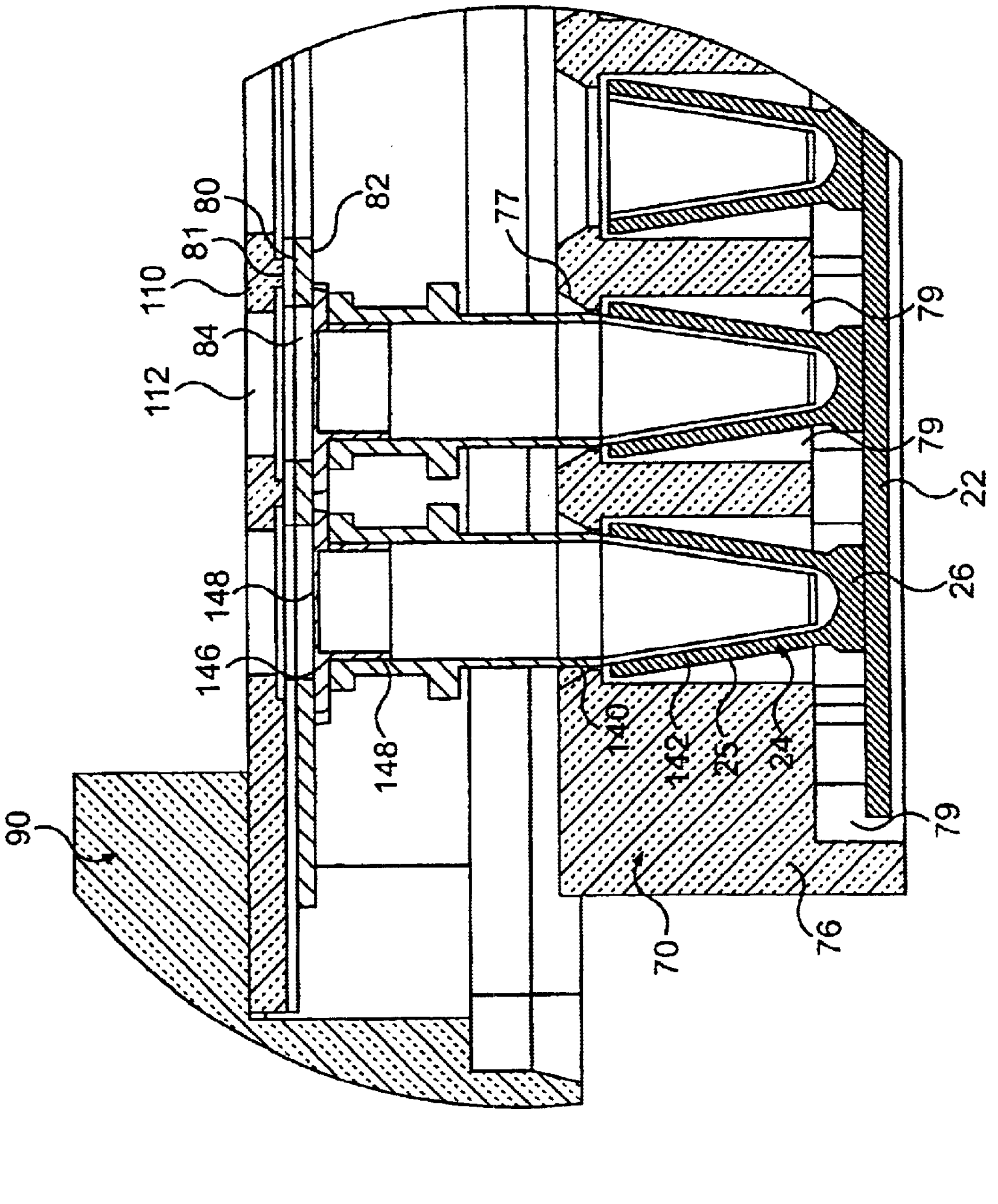
FIG. 5 is a partial front sectional view of the apparatus of FIG. 1 with sample tubes included.
Figure 7:
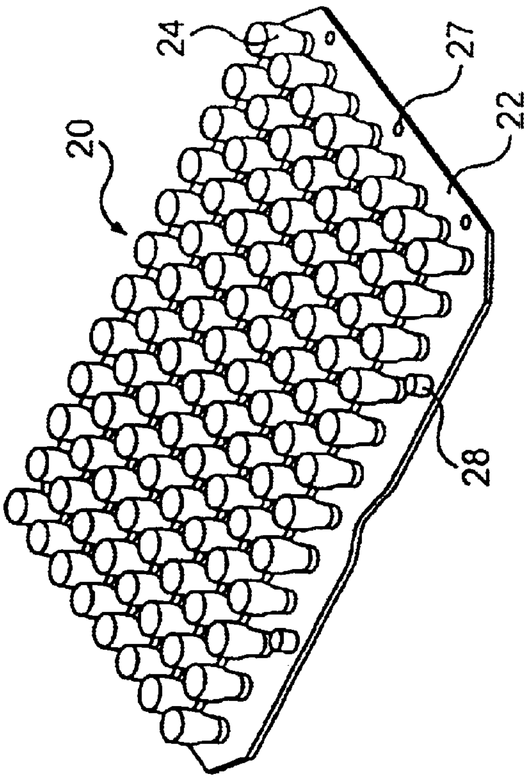
FIG. 7 is a perspective view of the thermal block assembly of FIG. 6.
Figure 6:
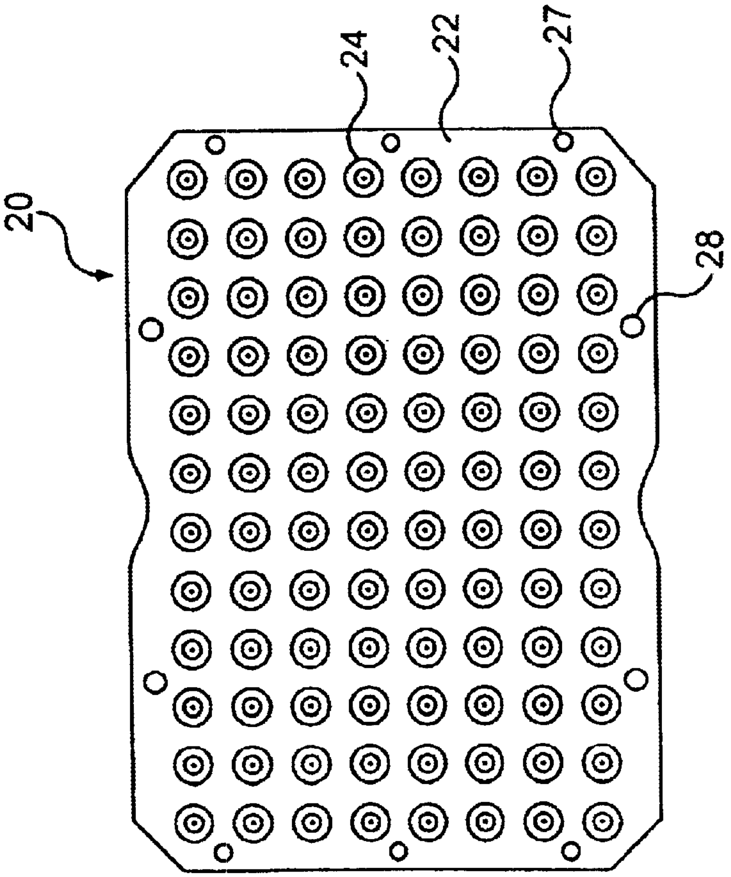
FIG. 6 is a top view of a thermal block assembly of the apparatus of FIG. 1.
Figure 8:
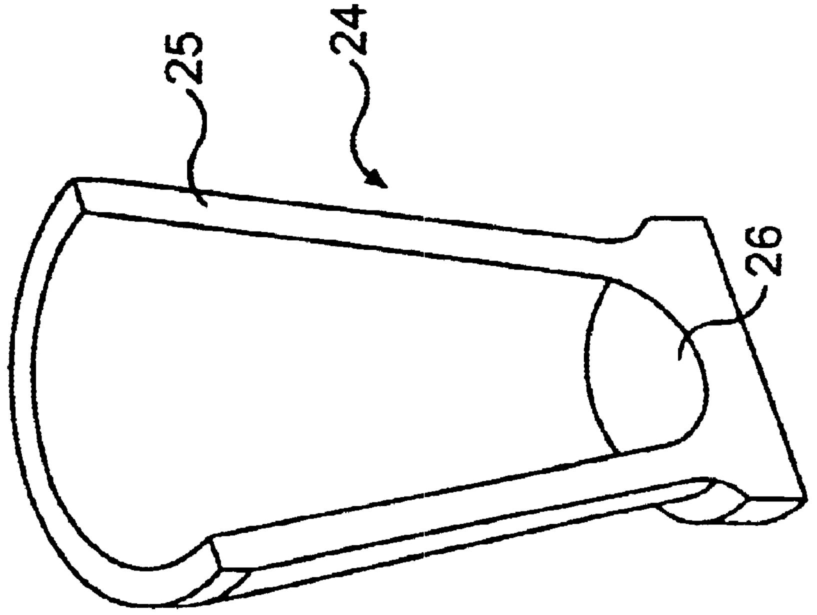
FIG. 8 is a perspective sectional view of a sample well of the apparatus of FIG. 1.
Figure 10:
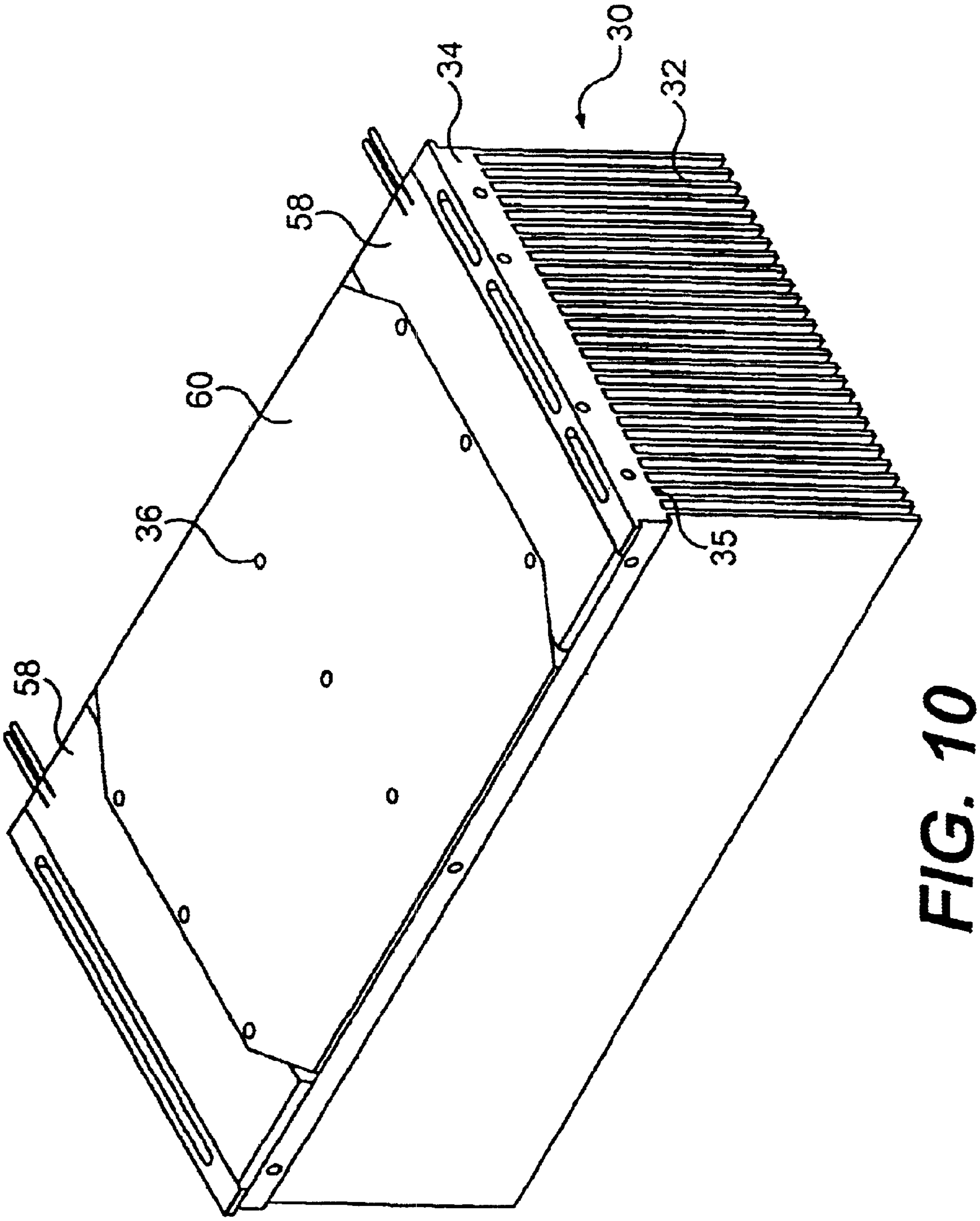
FIG. 10 is a perspective view of a heat sink of the apparatus of FIG. 1.
Figure 11:
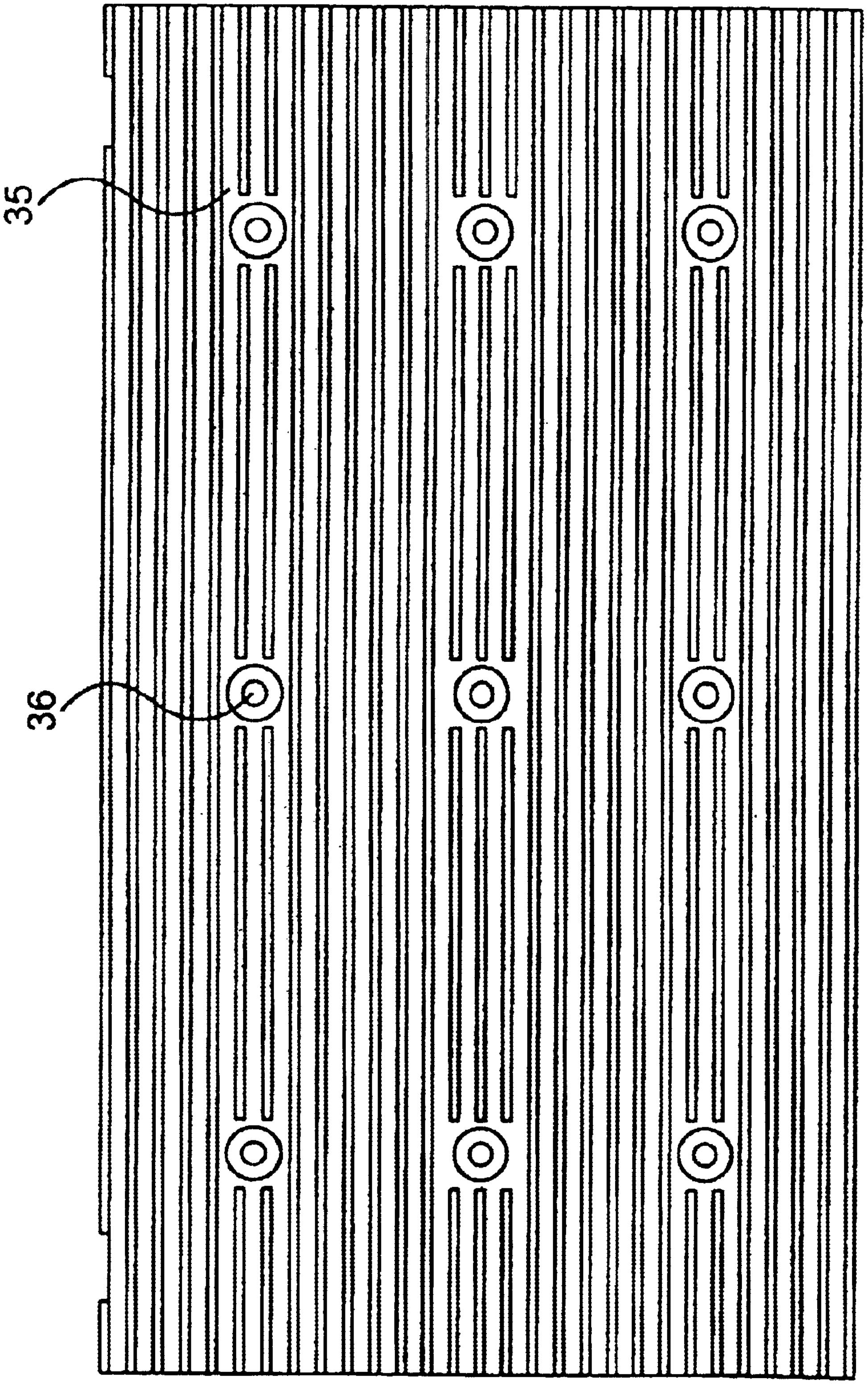
FIG. 11 is a bottom view of the heat sink of FIG. 10.
Figure 13:
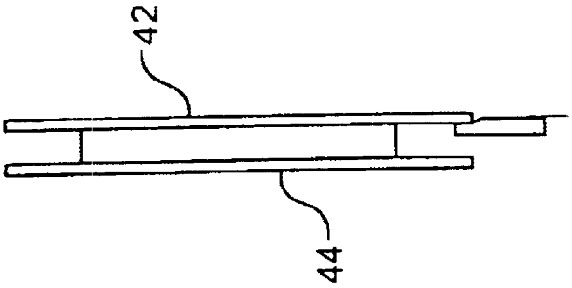
FIG. 13 is a side view of the solid state heater of FIG. 12.
Figure 14:
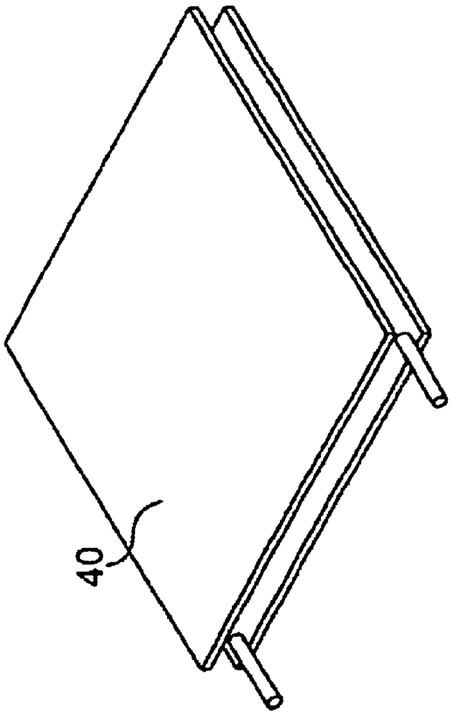
FIG. 14 is a perspective view of the solid state heater of FIG. 12.
Figure 12:
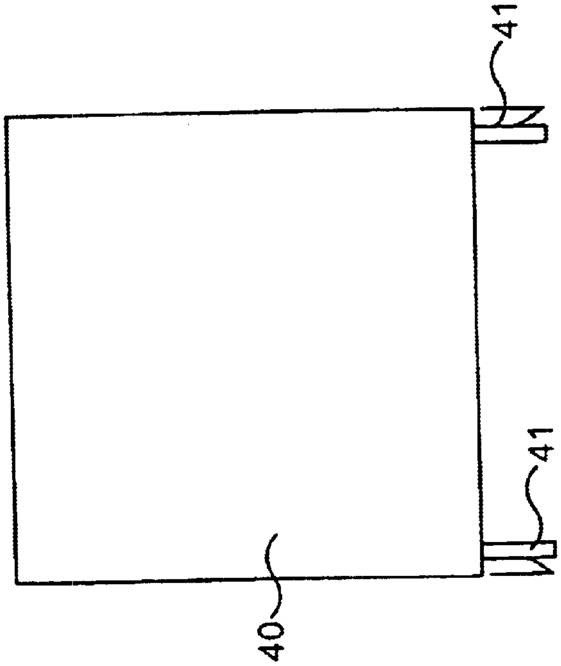
FIG. 12 is a top view of a solid state heater of the apparatus of FIG. 1.

In accordance with the present invention, an apparatus for thermally cycling samples of a biological material in the form of a biological reaction mixture such as DNA is provided. In accordance with the present invention, the apparatus includes a thermal block assembly including a plurality of sample wells for receiving sample tubes of a biological reaction mixture. As embodied herein and shown in FIGS. 1–8, the apparatus 10 for thermally cycling samples of DNA includes a thermal block assembly 20. Thermal block assembly 20 includes a flat thermal block plate 22 and a plurality of sample wells 24 for receiving tubes with samples of DNA, as best shown in FIGS. 2, 6 and 7. Thermal block plate 22 is substantially rectangular and is of sufficient size to accommodate a plurality of sample wells on the top surface, but could be of other shapes such as for example circular. In the embodiment shown in the drawings, the plate 22 accommodates 96 sample wells in an eight by twelve grid. It is to be understood that the number of sample wells can be varied depending on the specific application requirements. For example, the sample wells could be arranged to form a grid which is sixteen by twenty-four, thereby accommodating 384 sample wells. The sample wells 24 are conical in shape, as shown in FIG. 8. The walls 25 of the tube are conical, and extend at an angle to the flat plate 22. The bottom 26 of the interior of the sample well is rounded. The bottom of each sample well is attached to the thermal block plate 22. It should be understood that the sample wells could have any number of shapes, such as for example, cylindrical, so that the inner surface of the sample wells closely mates with the sample tube inserted inside.

The sample wells are designed so that plastic sample tubes with DNA samples can be placed in the sample wells. FIG. 5 shows a partial cut-away cross section with sample tubes 140 placed in the sample wells 24. Each sample well 24 is sized to fit the sample tube 140 exterior so that there will be substantial contact area between the plastic sample tube 140 and the interior portion of the sample well wall 25 to enhance the heat transfer to the DNA sample in the plastic sample tube and reduce differences between the DNA mixture and sample well temperatures. The plastic sample tube includes a conical wall portion 142 which closely mates with the sample well wall 25.

The plastic sample tubes are available in three common forms in the preferred embodiment: 1) single tubes; 2) strips of eight tubes which are attached to one another; and 3) tube trays with 96 attached sample tubes. The apparatus is preferably designed to be compatible with any of these three designs. A typical sample tube has a fluid volume capacity of approximately 200 $\mu$l, however other sizes and configurations can be envisaged. The fluid volume typically used in an experiment is substantially less than the 200 $\mu$l sample tube capacity.

Although the preferred embodiment uses sample wells, other sample holding structures such as slides, partitions, beads, channels, reaction chambers, vessels, surfaces, or any other suitable device for holding a sample can be envisaged. Moreover, although the preferred embodiment uses the sample holding structure for biological reaction mixtures, the samples to be placed in the sample holding structure are not limited to biological reaction mixtures. Samples could include any type of product for which it is desired to heat and/or cool, such as cells, tissues, microorganisms or non-biological product.

As embodied herein and shown for example in FIG. 5, each sample tube 140 also has a corresponding cap 146 for maintaining the biological reaction mixture in the sample tube. The caps 146 are typically inserted inside the top cylindrical surface 148 of the sample tube 140. These caps are relatively clear so that light can be transmitted through the cap. Similar to the sample tubes 140, the caps 146 are typically made of molded polypropylene, however, other suitable materials are acceptable. Each cap 146 has a thin, flat, plastic optical window 148 on the top surface of the cap. The optical window in each cap allows radiation such as excitation light to be transmitted to the DNA samples and emitted fluorescent light from the DNA to be transmitted back to an optical detection system during cycling.

A biological probe can be placed in the DNA samples so that flourescent light is transmitted in and emitted out as the strands replicate during each cycle. A suitable optical detection system can detect the emission of radiation from the sample. The detection system can thus measure the amount of DNA which has been produced as a function of the emitted flourescent light. Data can be provided from each well and analyzed by a computer.

The thermal block plate 22 is provided with mounting holes 27, as best shown in FIGS. 6 and 7. Attachment screws or other fasteners pass through each of the holes 27. The arrangement of these fasteners will be discussed in greater detail below.

Figure 9:
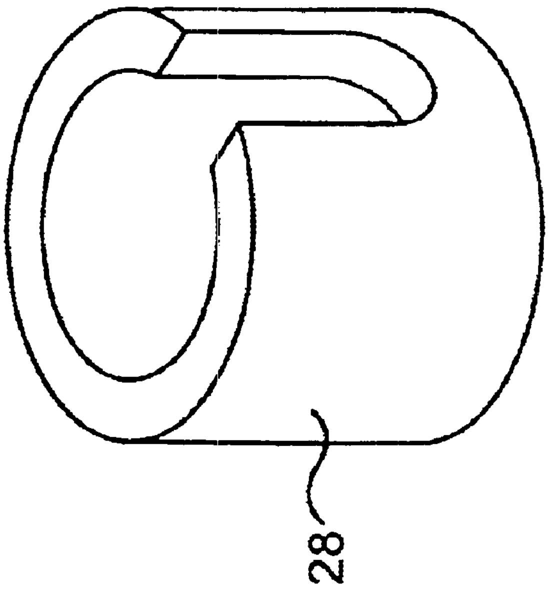
FIG. 9 is a perspective view of a sensor cup of the apparatus of FIG. 1.

The thermal block assembly 20 further includes a plurality of sensor cups 28, as best shown in FIGS. 6, 7 and 9. The sensor cups 28 are positioned adjacent the outer periphery of the thermal block plate 22. In the illustrated embodiment, four sensor cups 28 are positioned outside the grid of sample wells 24. There is at least one sensor cup for each thermoelectric or solid state heating device used to heat the thermal block assembly. The details of the solid state heating devices will be discussed below. In the illustrated embodiment, the apparatus is provided with four solid state heating devices, therefore it is appropriate to use at least four thermal sensors. If more solid state heating devices were used, then it would be desirable to have more sensor cups. Each of the solid state heating devices may heat at slightly different temperatures, therefore the provision of a thermal sensor in a sensor cup 28 for each solid state heater increases thermal block temperature uniformity.

The sensor cups 28 each include a thermistor or other suitable temperature sensor positioned to measure the temperature of the thermal block plate. Alternate temperature sensors include thermocouples or RTDs. Each type of temperature sensor has advantages and disadvantages. The temperature of the thermal block plate at the sensor cup corresponds to the temperature of adjacent sample wells. The temperature data from the cup is sent to a controller which will then adjust the amount of heat provided by the heating devices.

The thermal block plate 22, sample wells 24, and sensor cups 28 are preferably composed of copper alloy with a finish of electroplated gold over electroless nickel, although other materials having a high thermal conductivity are also suitable. This composition increases the thermal conductivity between the components and prevents corrosion of the copper alloy, resulting in faster heating and cooling transition times. It is important for the thermal block assembly to have a thermal conductivity chosen to increase the temperature uniformity of the sample wells. As previously discussed, increasing thermal block temperature uniformity increases the accuracy of the DNA cycling techniques. It is desirable to obtain substantial thermal block temperature uniformity among the sample wells. For example, in a thermal block assembly with 96 sample wells with 200 $\mu$l capacity sample wells being used to thermally cycle samples of DNA, it is typically desirable to obtain temperature uniformity of approximately plus or minus 0.5 degrees C.

The sample wells 24 and sensor cups 28 are fixed to the top surface of the thermal block plate. In preferred embodiment, the sample wells 24 and sensor cups 28 are silver brazed to the thermal block plate 22 in an inert atmosphere, although other suitable methods for fixing the sample wells and sensor cups are known. For example, the design of the present invention is well suited for a fixing method involving ultrasonic welding. In this ultrasonic welding method, the sample wells are attached to the thermal plate using pressure and mechanical vibration energy. Many copper alloys and other non-ferrous alloys are well suited for this method. Ultrasonic welding provides the advantages of excellent repeatability and minimal impact to the original material properties because no significant heating is required. Another sample well fixing method involves a copper casting process. Copper casting would require design changes in the sample well geometry. Although the casting process would be less expensive than the silver brazing method, there will be a loss in performance. Therefore, the silver brazing method described above is the preferred method for fixing the sample wells to the thermal block plate.

In accordance with the present invention, the apparatus further includes a heat sink for transferring heat from the thermal block assembly to ambient air located adjacent to the heat sink. As embodied herein and shown in FIGS. 1–4 and 10–11, heat sink 30 is provided for transferring heat from the thermal block assembly 20. Heat sink 30 includes a plurality of parallel, rectangular fins 32 extending downward from a base 34. It should be understood that the heat sink 30 may be of any well-known type. The heat base 34 and rectangular fins 32 are preferably made from aluminum, although other suitable materials may be used. The heat sink 30 allows the thermal block assembly 20 to be quickly and efficiently cooled during thermal cycling. Heat is transferred from the thermal block assembly 20 to the heat sink 30 due to the heat sink's lower temperature. The heat which flows to the heat sink is dissipated from the heat sink rectangular fins 32 to the ambient air which flows between the fins.

The heat sink base 34 includes attachment holes 36 through which fasteners such as attachment screws pass. The attachment holes 36 extend from the top surface 60 to the bottom surface or underside 35 of the heat sink base 34. The details of the attachment means will be described later.

In accordance with the present invention, the apparatus further includes at least one solid state heater to provide heat to the thermal block assembly. As embodied herein and shown in FIGS. 2, 4, 12–15, and 18–19, solid state heaters 40 are provided in order to supply heat to the thermal block assembly. The solid state heaters 40 are preferably thermoelectric heaters such as Peltier heaters, but could also be any other type of heater such as a resistive heater. Peltier heaters are preferred because they can be controlled to exhibit a temperature gradient, as will be discussed later. The other advantage of Peltier heaters is that Peltier heaters are capable of providing cooling. The Peltier heaters can be controlled to cool the thermal block assembly below the ambient temperature. This cooling is not possible with other types of heaters such as a resistive element heater. This cooling allows the Peltier heaters to pump heat from the thermal block assembly to the heat sink. The Peltier heaters achieve cooling by changing the electrical current polarity into the Peltier heaters. The convective air current across the heat sink transfers this heat which has been pumped to the heat sink to the ambient air.

Each Peltier heater includes two lead wires 41 for supplying an electrical current through the heater. Each Peltier heater also includes a first side 42 located closer to the thermal block plate 22, and a second side 44 located closer to the heat sink base 34. During heating of the Peltier heater, the first side 42 will be hot and the second side 44 will be cool. During cooling by the Peltier heater, the first side 42 will be cool and the second side 44 will be hot. As previously discussed, the hot and cold sides are changed with the reversal of the current flow. A plurality of these heaters are located between the heat sink 30 and thermal block assembly 20. The number of Peltier heaters can vary depending on the specific heating and cooling requirements for the particular application. In the illustrated embodiment, four Peltier heaters are provided. The number and shape of Peltier heaters can be modified. The system could be altered such that a rectangular Peltier heater could be used, alone or in combination with other rectangular or square Peltier heaters. Other shapes of Peltier heaters could also be envisaged. Other types of Peltier heaters, such as two-stage Peltier heaters, could also be envisaged. For example, a two-stage Peltier heater has two levels or stages of heat pumping elements which are separated by a plate. These two-stage Peltier heaters are typically used in order to create very large temperature differences between the cold and hot sides. Peltier heaters with more than 2 pumping stages are also possible.

As previously discussed, each of the Peltier heaters is controlled independently of the other Peltier heaters. Independent heater control is desirable because each Peltier heater may have slightly different temperature characteristics, that is, if identical currents were placed in each of the Peltier heaters, each of the Peltier heaters could have a slightly different temperature response. Therefore, by providing temperature control using multiple sensors and sensor cups for the heaters, each Peltier heater can be separately controlled to enhance uniform temperature distribution to the thermal block assembly. Alternately, the independent temperature control can be used to set up a plurality of temperature zones with different temperatures.

In accordance with the present invention, the apparatus further includes a spacer, such as a bracket for positioning the at least one solid state heater. As embodied herein and shown in FIGS. 2, 4, and 15–17, the spacer bracket 46 is provided above and adjacent to the heat sink base 34. The spacer bracket is preferably composed of polyetherimide, although other suitable materials are also acceptable. A spacer bracket cover 49 is included above and adjacent to the spacer bracket 46. The spacer bracket 46 includes attachment holes 48 through which fasteners such as the attachment screws pass.

Figure 15:
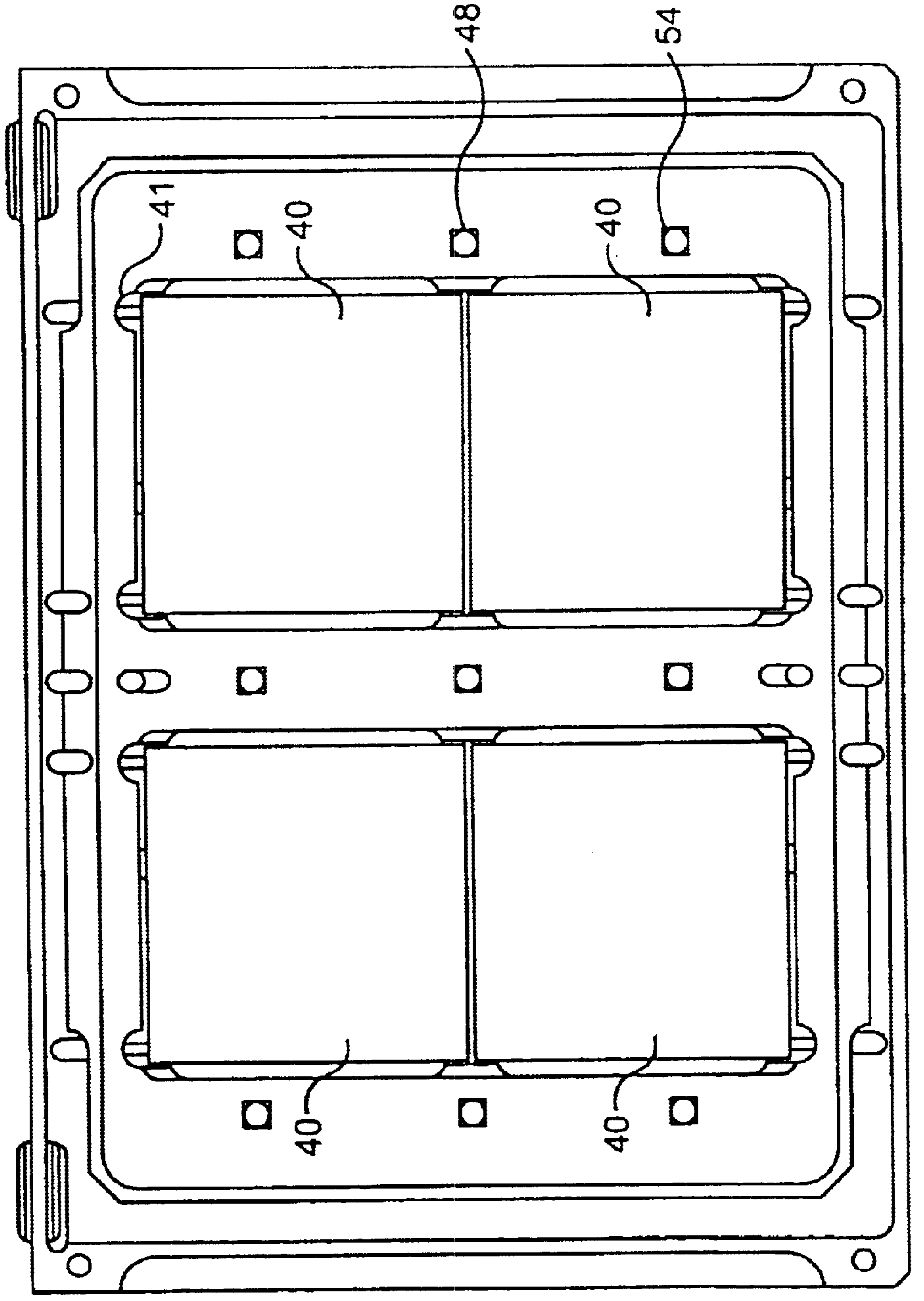
FIG. 15 is a top view of a spacer bracket with the solid state heaters of FIGS. 12–14 installed.
Figure 16:
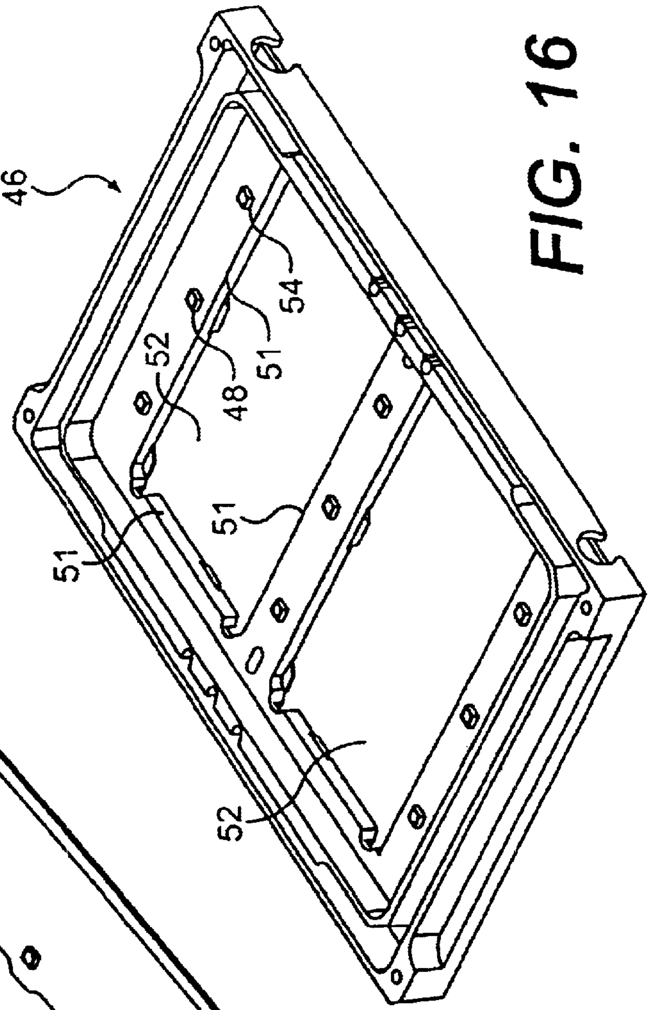
FIG. 16 is a top perspective view of the spacer bracket of the apparatus of FIG. 1.
Figure 17:
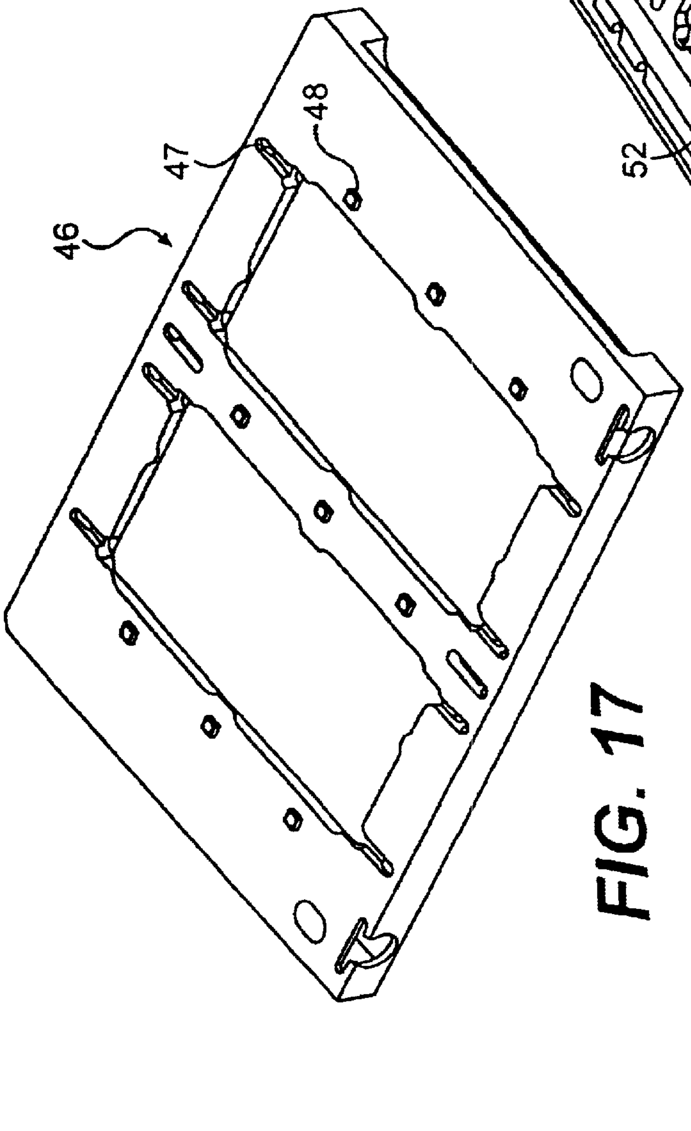
FIG. 17 is a bottom perspective view of the spacer bracket of FIG. 16.

The spacer bracket 46 includes openings 52 in which the Peltier heaters 40 are positioned. As shown in FIG. 15, for example, two Peltier heaters 40 can be positioned in each of the two openings 52. The lead wires 41 of the Peltier heaters are positioned so that they will be received in slots 47 of the spacer bracket. The placement of the lead wires 41 in the slots 47 will prevent significant movement by the Peltier heaters in the bracket, while still allowing slight movement. The slots 47 are dimensioned to be slightly larger than the lead wires 47 to allow such slight movement.

The spacer bracket has bosses 54 around the attachment holes 48 which have a thickness such that the thermal block assembly will be placed in compression. By placing the thermal block assembly in compression, heat transfer can occur more efficiently. For example, by imparting a compressive force, the Peltier heaters, heat sink, thermal block plate, and thermal interface materials will be placed firmly in contact with one another. It should be understood that the spacer bracket can be designed to accommodate a variety of different Peltier heater configurations. The spacer bracket and Peltier heaters are designed so that a minimum amount of heat is transferred to the spacer bracket. As shown in FIG. 15, a small gap is provided between the outside edge of the Peltier heaters 40 and the inner surfaces 51 of the inner walls of the openings 52. The gap reduces the amount of contact between the Peltier heaters and the spacer bracket, thereby reducing the amount of heat loss to the spacer bracket.

In accordance with the present invention, the apparatus further includes a heater located below the solid state heaters for heating a bottom portion of the solid state heaters. As embodied herein and shown in FIGS. 2, 10 and 18, a plurality of resistive element heaters 58 are provided on the top surface 60 of the heat sink base 34. It should be understood that any other type of suitable heater may also be used. In the illustrated embodiment, resistive element heaters 58 are placed at the front and back edges of the top surface 60 of the heat sink. For the sake of the specification, the front of the apparatus is the portion of the apparatus located adjacent the air exit plate on the left side of the apparatus in FIG. 1. The back of the apparatus is the portion of the apparatus located adjacent the opposite air exit plate which cannot be seen in FIG. 1. The positioning of the front and the back resistive element heaters helps to provide thermal block temperature uniformity in a manner described in further detail below.

The Peltier heaters 40 are the primary source used for heating the thermal block plate 22. However, the Peltier heaters are primarily located towards the central portion of the apparatus, in that the Peltier heaters are located in the openings 52 of the spacer bracket 46 as best shown in FIGS. 15–18. Therefore, in the absence of the bottom resistive heater, the Peltier heaters would be directed primarily to the central portion of the thermal block plate, with the risk of decreasing temperatures at the edges of the thermal block plate, such as the front and back portions.

The apparatus of the present invention includes an arrangement for heating the thermal block at the front and back edges to provide thermal block temperature uniformity. Resistive heaters 58 are provided for improving thermal block plate temperature uniformity. The resistive heaters do this by heating the edges of the heat sink on which they are attached. This results in a desired temperature gradient in the heat sink 30. The resistive heaters 58 do not directly heat the front and back portions of the thermal block through convection or direct contact. The resistive heaters 58 also do not contact the Peltier heaters 40. The resistive heaters 58 create the temperature gradient in the heat sink by increasing the temperature of the heat sink at the front and back of the heat sink base 34. As a result of the temperature gradient on the heat sink, the Peltier heaters transfer a greater amount of heat at the front and back edges of the Peltier heater which are adjacent to the heat sink at the locations closest to the resistive heaters 58. The hot side of the Peltier heaters will have a hotter temperature at the portion of the Peltier heater closest to the resistive heater. Therefore, the front and back portions of the thermal block plate will receive a greater amount of heat transfer than the central portion of the thermal block plate. This will ensure that the front and back portions of the thermal block plate which are not adjacent to the Peltier heaters will receive heat transfer by conduction through the thermal block plate and thermal interface elements which will be discussed below. It should be understood that the number and position of the resistive element heaters is exemplary only and will vary depending on the design requirements of the apparatus.

In accordance with the present invention, at least one bottom thermal interface element is provided between the bottom of the Peltier heaters and the top surface of the heat sink. As embodied herein and shown in FIGS. 2 and 18, bottom thermal interface elements 62 are flat plates positioned between the bottom of the Peltier heaters 40 and the top surface 60 of the heat sink. A bottom thermal interface element 62 is provided for each of the openings 52 in the spacer element. Therefore, the two Peltier heaters in the front opening are provided with a plate of thermal interface material, and the two Peltier heaters in the back opening are provided with a second plate of thermal interface material.

Figure 18:
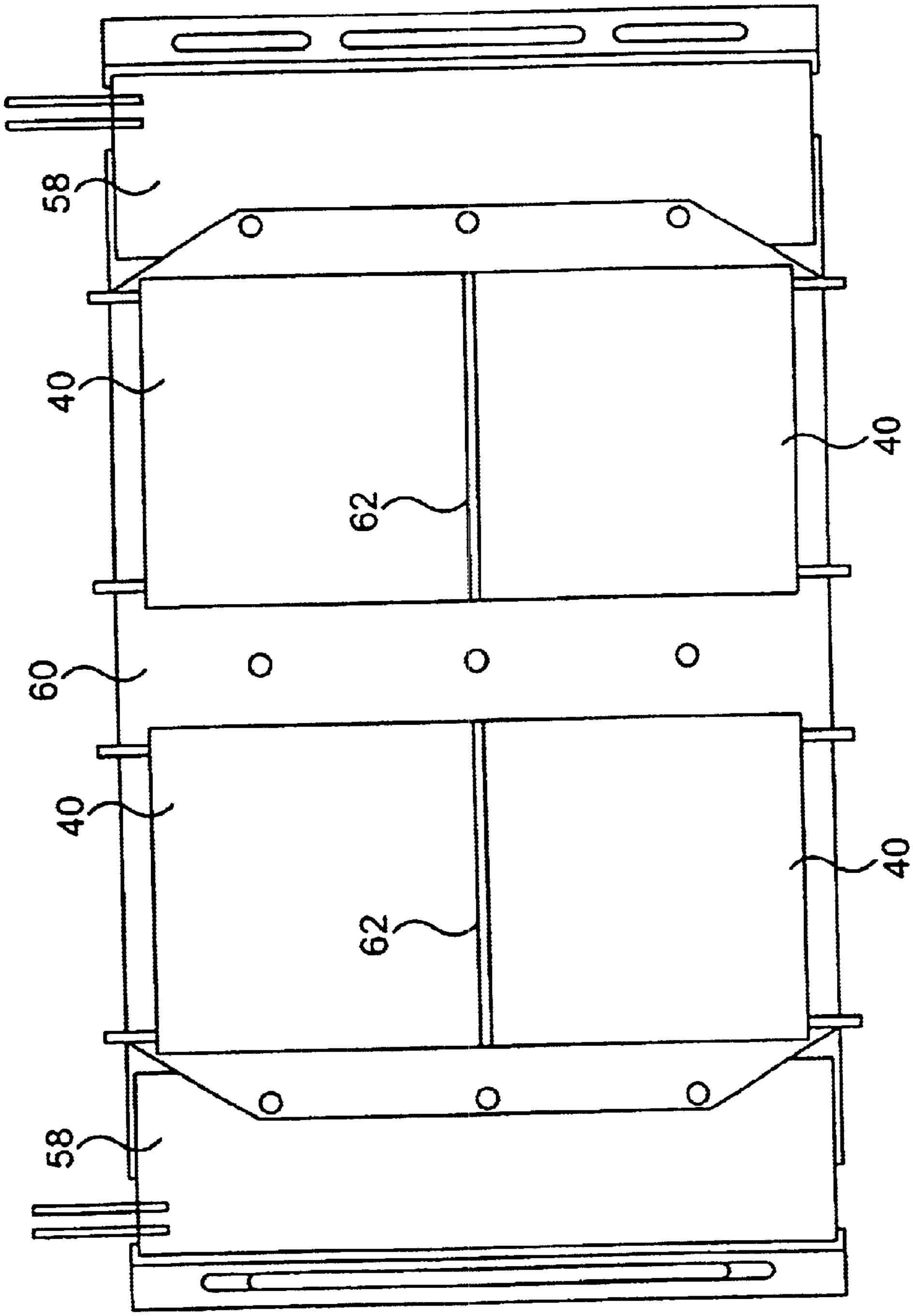
FIG. 18 is a top view of the heat sink, a bottom resistive heater, and the solid state heaters of the apparatus of FIG. 1.
Figure 19:
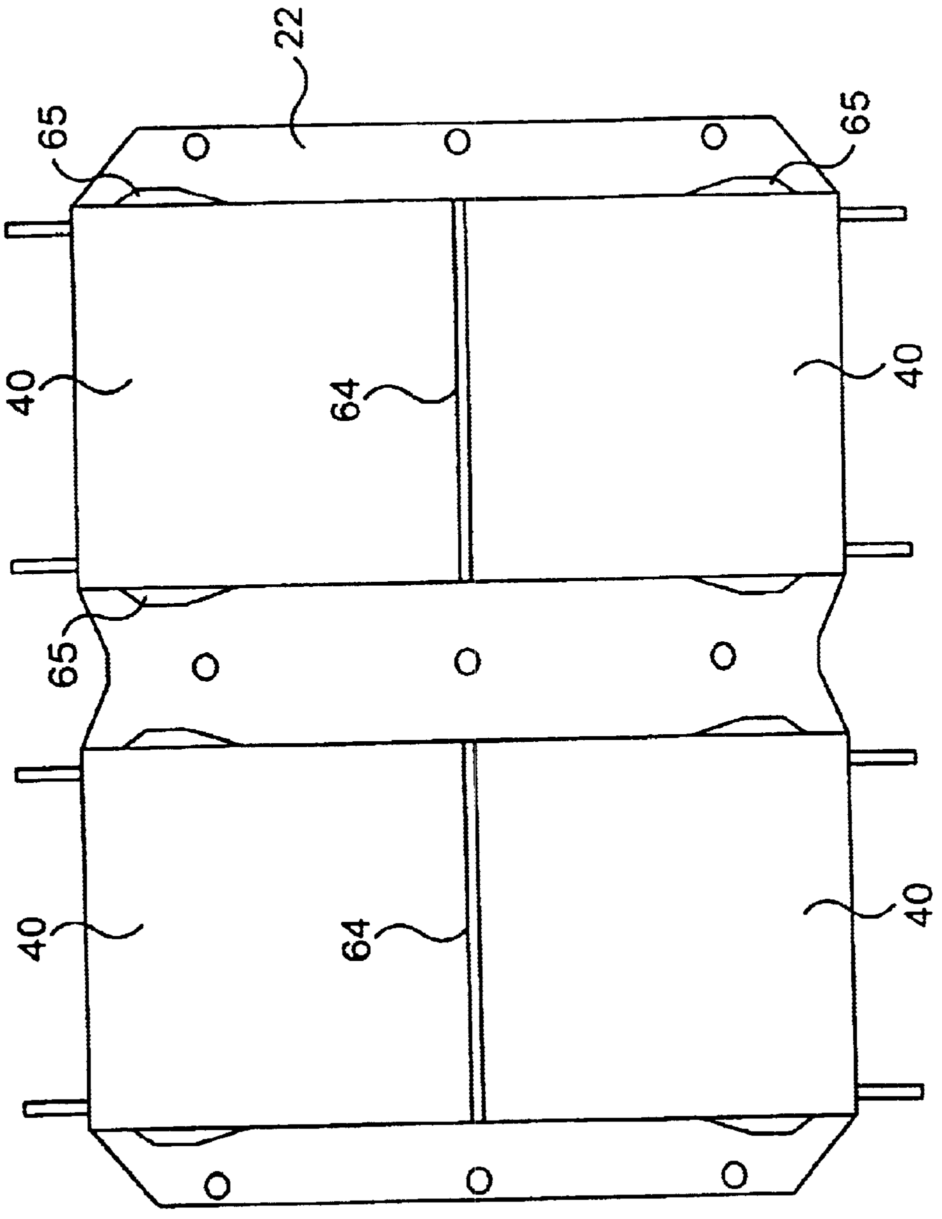
FIG. 19 is a bottom view of a thermal block plate and the solid state heaters of the apparatus of FIG. 1.

Each bottom thermal interface element 62 is slightly smaller than its respective opening 52 in the spacer element. Each bottom thermal interface element roughly corresponds to the size of the surface area of the two Peltier heaters which it covers. For example, in the top view shown in FIG. 18, the bottom thermal interface elements are located immediately underneath the Peltier heaters. Only a small portion of the bottom thermal interface element can be shown because the Peltier heaters cover the entire surface area of the bottom thermal interface elements except for the portion located in between the two Peltier heaters sharing the same opening, as shown in FIG. 18.

The bottom thermal interface elements 62 have a high rate of thermal conductivity in order to provide effective heat transfer between heat sink and Peltier heaters. In addition, the material is relatively soft so that the plates 62 can be compressed. This allows the Peltier heaters to have a more evenly distributed surface area with the top of the heat sink. An example of the type of material to be used in the thermal interface elements is a boron nitride filled silicone rubber. Any other type of suitable material is also acceptable.

In accordance with the present invention, at least one top thermal interface element is provided between the top of the Peltier heaters and the bottom of the thermal block plate. As embodied herein and shown in FIGS. 2 and 19, a pair of top thermal interface elements 64 are located between the top of the Peltier heaters and the bottom of the thermal block plate 22. During heating by the Peltier heaters, the top thermal interface elements conduct the heat from the first side 42 of the Peltier heaters 40 to the bottom of the thermal block plate 22. The top thermal interface elements 64 are similar in shape and size to the bottom thermal interface elements 62, except for the additional provision of thermal interface wings 65 on the thermal interface elements. The wings are located on the front and back side of each Peltier heater. The wings 65 provide heat transfer to the areas of the thermal block plate 22 outside of the Peltier heaters. The wings 65 effectively conduct the additional heat that is generated in the heat sink and Peltier heaters at the front and back edges due to the bottom resistive heaters. The wings distribute this heat to the front and back edges of the thermal block plate. This increases thermal block temperature uniformity. The top thermal interface elements 64 are composed of the same material with the relatively high rate of thermal conductivity as the bottom thermal interface elements 62.

It should be understood that any number of interface elements, including only one, could be used. The provision of the top and bottom thermal interface elements also allows the Peltier heaters 40 to "float" between the thermal block plate 22 and the heat sink base 34. The compressible thermal interface material provides for effective heat transfer among the surfaces while also uniformly loading the Peltier heaters in compression. The use of the compressible thermal interface material increases cycle life and reliability of the Peltier heaters. The thermal interface material improves the reliability of the system by affecting the compressive load imparted onto each Peltier heater. Any structural compressive loading forces are dampened and uniformly distributed into the Peltier heaters due to the thickness and elastomeric characteristics of the thermal interface material. Due to the more uniform loads imparted on the Peltier heaters, the reliability of the solder joints within each Peltier heater will be improved. It is important not to overly compress the Peltier heater with physical or thermal shock which can result in premature failure. Other ways in which the present invention improves the reliability of the Peltier heaters will be discussed below.

In accordance with the present invention, the apparatus further includes a first insulating cover for insulating the thermal block assembly. As embodied herein and shown in FIGS. 2, 4, 5, and 20–22, first insulating cover 70 is provided for insulating the thermal block assembly 20. The first insulating cover is preferably composed of polyetherimide, although other suitable materials are also acceptable. First insulating cover 70 is in the shape of a block having an inner surface 72 with a plurality of cylindrical sample well openings 74. Each sample well opening 74 corresponds to a sample well 24 on the thermal block assembly 20. When the first insulating cover 70 is placed on top of the thermal block assembly 20, the sample wells 24 are encapsulated within their respective sample well opening 74. As shown in FIG. 2, the depth of the sample wells openings 74 is almost as long as the sample wells 24. In the illustrated embodiment, the cylindrical opening 74 extends for a substantial length of the sample well positioned inside the cylindrical opening. Therefore, the sample wells 24 are almost completely surrounded by the first insulating cover.

The first insulating cover 70 achieves the insulation of the sample wells of the thermal block assembly in two main ways. First, the insulating cover substantially surrounds the thermal block assembly, thereby minimizing the difference in temperature between the thermal block assembly and air 79 in and around the thermal block assembly, as best shown in FIG. 5. The first insulating cover 70 reduces the amount of air surrounding the thermal block assembly. Second, the first insulating cover 70 reduces the convective heat transfer coefficient along the thermal block assembly surfaces because the first insulating cover reduces the amount of natural convective air currents.

Figure 20:
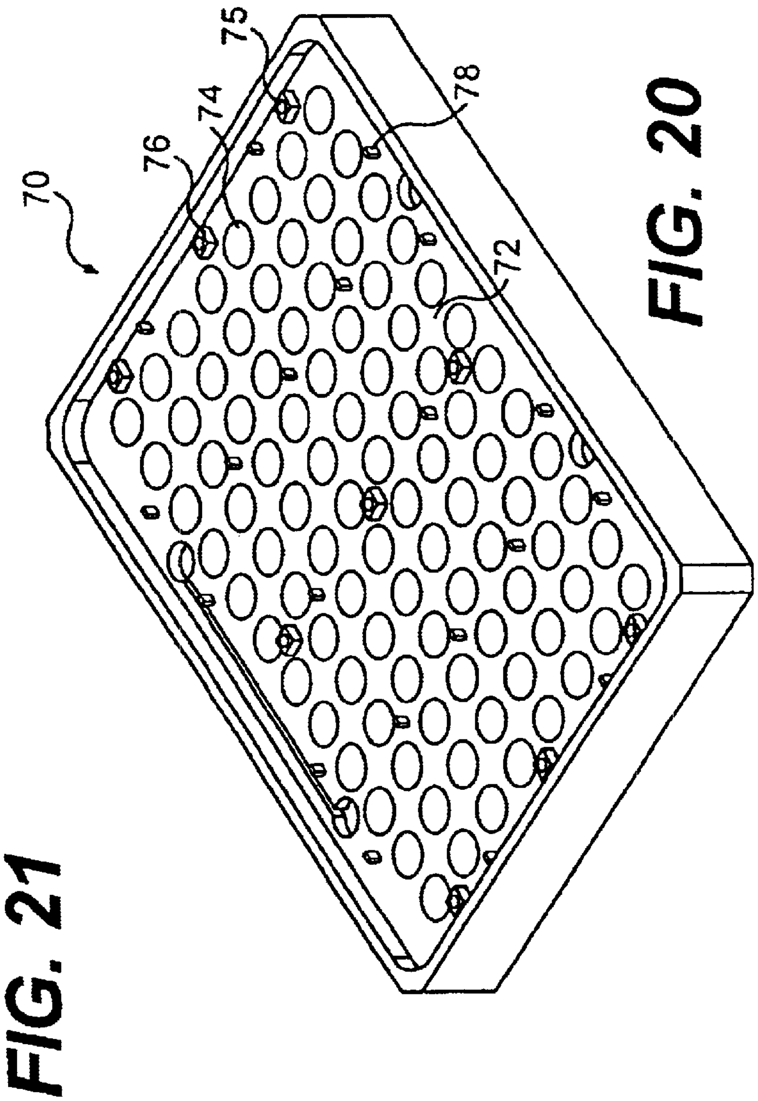
FIG. 20 is a bottom perspective view of a thermal block assembly insulating cover of the apparatus of FIG. 1.
Figure 21:
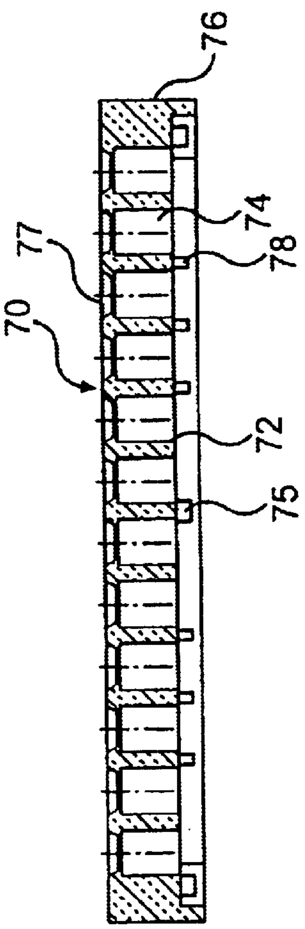
FIG. 21 is a side sectional view of the thermal block assembly insulating cover of FIG. 20.
Figure 22:
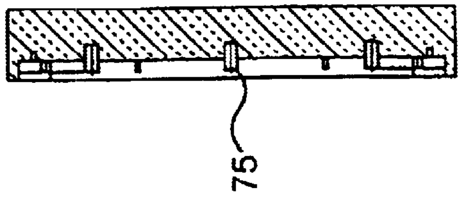
FIG. 22 is a front sectional view of the thermal block assembly insulating cover of FIG. 20.

The first insulating cover further includes tube holes 77. Tube holes 77 are provided at the end of each sample well opening 74. Each tube hole 77 accommodates the passage of a sample tube 140 into a sample well as best shown in FIG. 5. As shown in FIGS. 20–22, the first insulating cover further includes projections 78. The projections 78 are located at predetermined locations of the inner surface 72 of the first insulating cover in order to provide proper spacing between the interior surface of the first insulating cover and the top surface of the thermal block plate 22. The projections 78 are also sized and located in order to provide adequate pressure between the thermal block assembly and the thermal interface material. The projections 78 contact the top surface of the plate 22.

The first insulating cover 70 further includes a plurality of bosses 76 with attachment holes 75 for passage of the attachment screws. The attachment holes extend partly into the first insulating cover as shown in FIG. 22.

The means for attaching the various components described above will now be described. It is important that the means for attaching the various components does not result in significant heat transfer away from the thermal block assembly to the outside of the components. Any heat transfer which occurs from the thermal block assembly should occur through the thermal block plate, thermal interface elements, solid state heaters and heat sink in order to maximize temperature uniformity. These elements are designed to have uniform heating and cooling characteristics so that no one area of the thermal block plate will be cooled any faster than another area. However, attachment fasteners must be provided in order to attach the first insulating cover, thermal block plate, thermal interface elements, spacer bracket, Peltier heaters, and heat sink base. The attachment fasteners of the present invention have been designed to minimize the heat transfer that occurs through the attachment fasteners.

Figure 23:
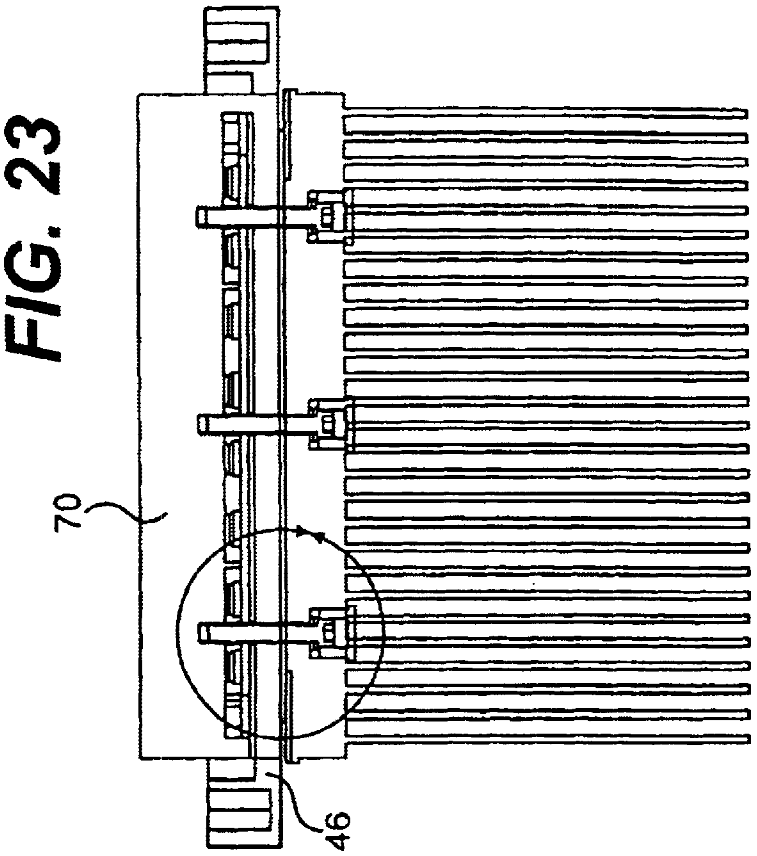
FIG. 23 is a side sectional view along a plurality of attachment screws of the apparatus of FIG. 1.
Figure 24:
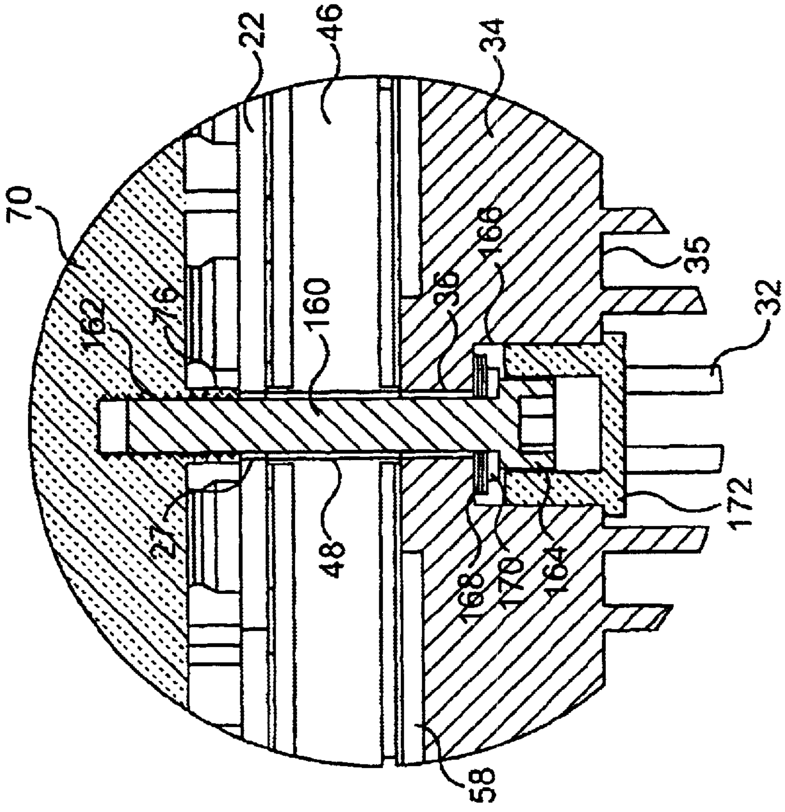
FIG. 24 is a magnified view of a portion of FIG. 23.

As embodied herein and shown in FIGS. 23 and 24, a plurality of attachment screws 160 are provided for passage through the various attachment holes. Each attachment screw includes a threaded portion and a head 164 in order to impart a compressive force on the attachment screw and the components between the first insulating cover 70 and the heat sink. The threaded portion of each screw 160 threads into an internal threaded portion 162 of the first insulating cover 70. The internal threaded portion 162 of the first insulating cover 70 extends from the boss 76 on the inside surface 72 of the first insulating cover. Each attachment screw then passes through the spaces between the sample wells, through the attachment hole 27 in the thermal block plate 22, through the attachment hole 48 in the spacer bracket 46, and through the attachment hole 36 in the heat sink base 34. As can be seen in the drawings, the attachment screw preferably passes through holes 27, 48 and 36 without making contact with the sides of the attachment holes. The attachment screw 160 is preferably made out of stainless steel, although any number of suitable materials are also acceptable. A bore 166 is provided on the underside of the heat sink underside 35 for the head 164 of the attachment screw 160. By providing the bore 166 on the underside 35 of the heat sink, the attachment screw is spaced from the convection currents which occur along the underside of the heat sink.

The means for attaching the various components further includes an insulating washer 168 positioned between the underside 35 of the heat sink base and the head of the screw. The insulating washer is preferably made out of mylar, although other materials with good insulating properties are also acceptable. The mylar washer prevents the attachment screw from making contact with the heat sink 30. This lack of contact prevents heat from the thermal block plate 22 from being transferred to the heat sink 30 via the attachment screws. This is especially important because the heat sink 30 is normally at a lower temperature than the thermal block plate 22. As shown in FIGS. 23 and 24, a standard split locking washer 170 may also be provided between the surfaces of the insulating washer 168 and the attachment screw head 164. The split locking washer 170 helps to maintain the screw torque and preload during the thermal cycling.

A plastic screw cap 172 is provided for plugging the bore 166. The plastic screw cap 172 surrounds the head 164 of the attachment screw, and helps to prevent heat from being transferred from the head of the attachment screw to the ambient air that flows along the underside of the heat sink. Insulating screw caps 172 are therefore provided over the top of each attachment screw head in order to prevent heat transfer to the ambient air. These insulating screw caps can be made out of a variety of materials such as ethylene vinyl acetate.

Figure 25:
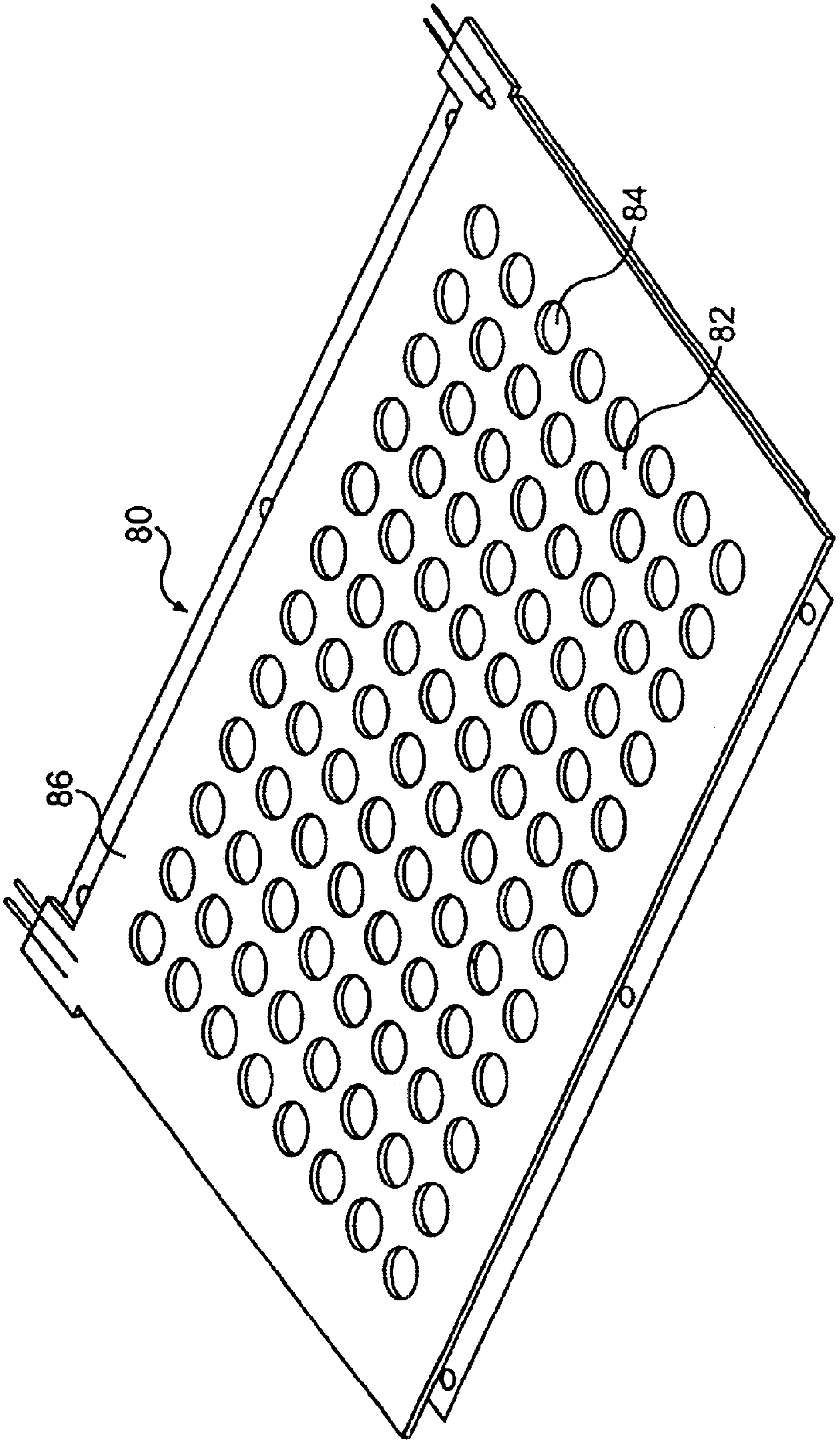
FIG. 25 is a bottom view of a top resistive element heater of the apparatus of FIG. 1.
Figure 26:
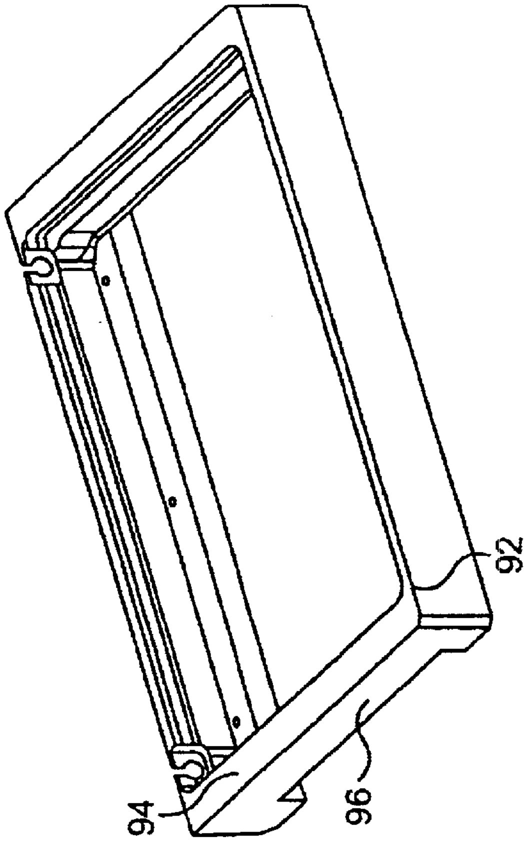
FIG. 26 is a perspective view of the top insulating cover of the apparatus of FIG. 1.
Figure 27:
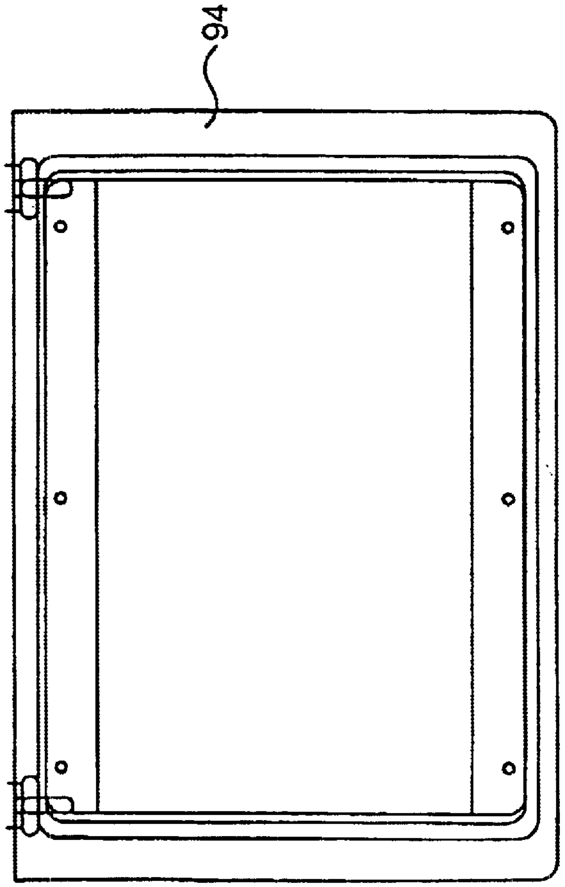
FIG. 27 is a bottom view of the top insulating cover of FIG. 26.
Figure 28:
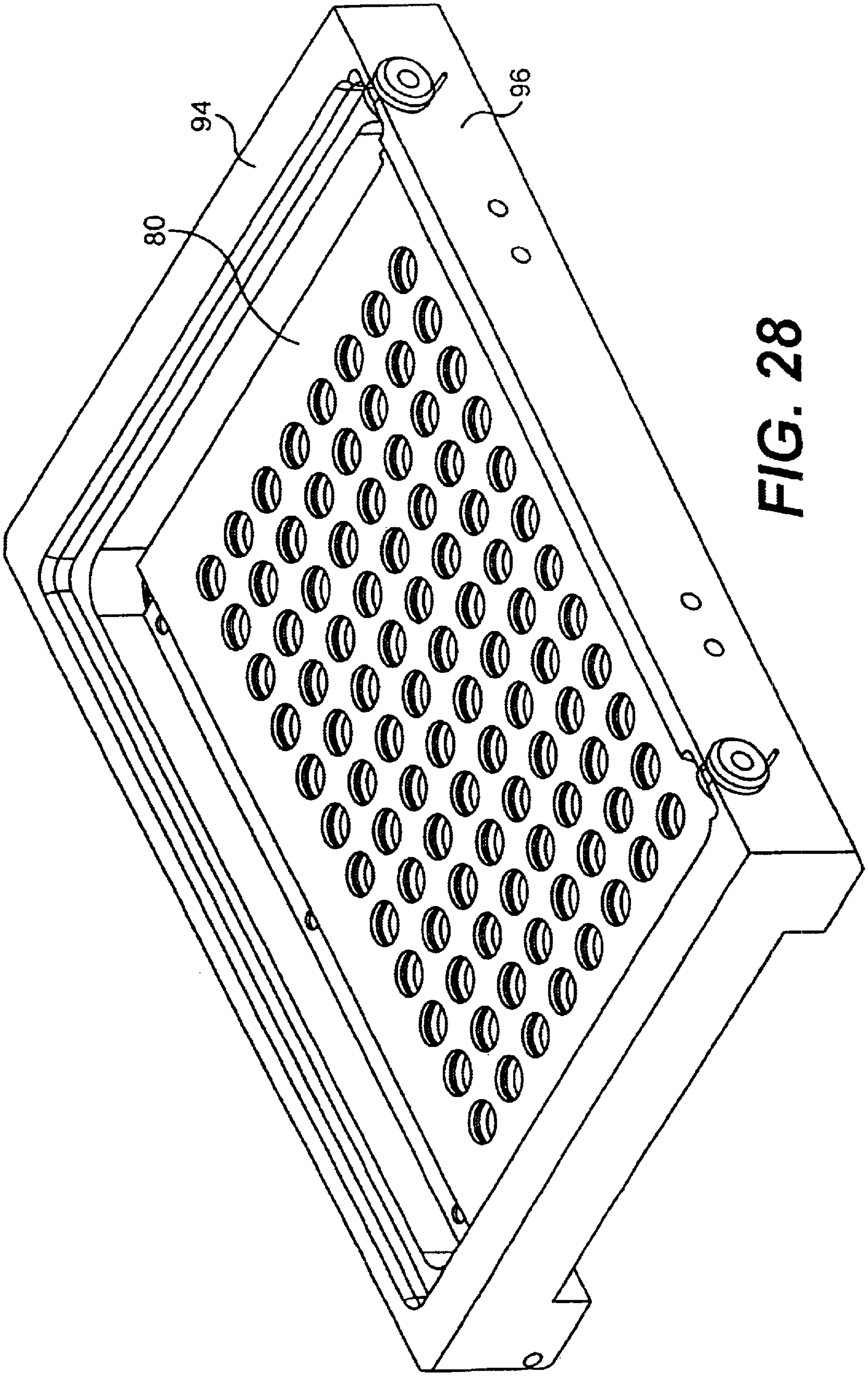
FIG. 28 is a perspective view of a top insulating cover assembly of the apparatus of FIG. 1.
Figure 30:
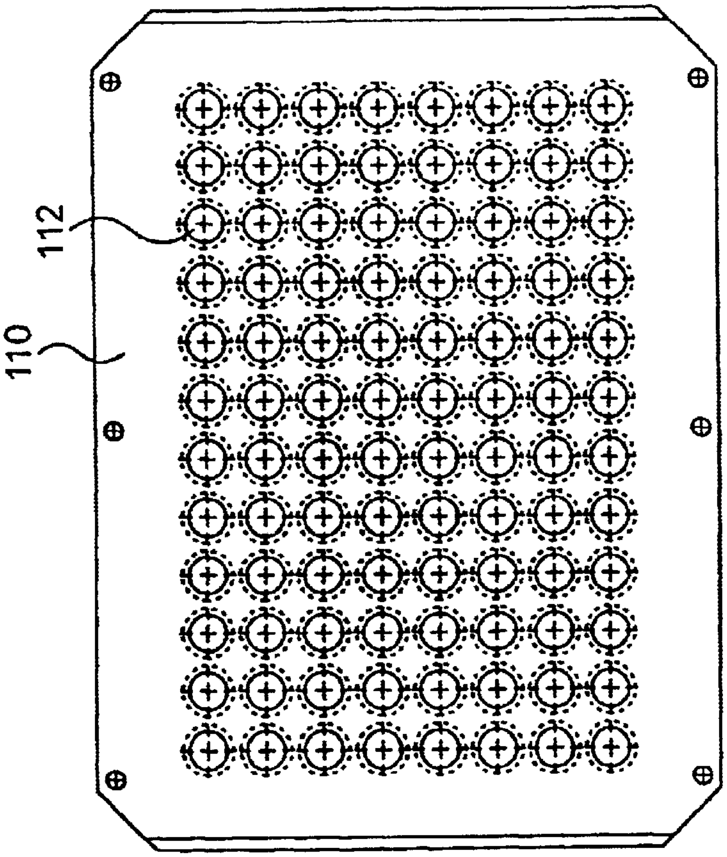
FIG. 30 is a top view of the top insulating plate of FIG. 29.
Figure 29:
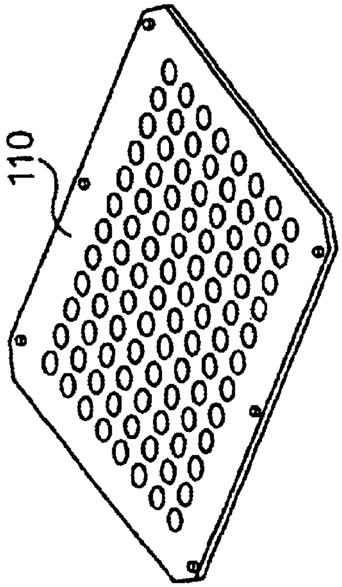
FIG. 29 is a perspective view of a top insulating plate of the apparatus of FIG. 1.

In accordance with the present invention, the apparatus further includes a resistive element heater located above the thermal block assembly to provide heat to the thermal block assembly. It should be understood that any other type of suitable heater may also be used. As embodied herein and shown in FIGS. 2, 5 and 25, top resistive element heater 80 is placed above the thermal block assembly 20. The top resistive element heater 80 is a flat rectangular plate as shown in FIG. 25, with a heating area 86 around the outside periphery. The surface of the plate is spaced from the top of the first insulating cover 70 so that the sample tubes 140 can be accommodated between the resistive element heater 80 and the first insulating cover 70 as best shown in FIG. 5.

The surface 82 of the resistive element heater has a plurality of holes 84 for allowing emitted radiation from the samples to pass out of the apparatus to be detected by a suitable detection system. The surface 82 of the resistive element heater is lined with a thin layer of insulating material such as silicone rubber. The thin insulating layer on the surface of the resistive element heater contacts the top of the caps 146 of the sample tubes 140 to reduce the likelihood of condensation occurring on the tops of the caps. This is best shown in FIG. 5. Condensation on the caps may increase errors in the data and degrade the accuracy of the experiment. The resistive element heater also imparts a compressive load on the sample tubes. This compressive load enhances the uniform contact between the outer surfaces of the sample tubes and the inner surfaces of the sample wells. The compressive load is imparted as a result of the securing means on the second insulating cover which will be discussed below.

An aluminum contact plate 81, shown for example in FIG. 5, is provided between the resistive heater element 80 and the second insulating cover which will be described below.

In accordance with the present invention, the apparatus further includes a second insulating cover including a securing means for securing the DNA sample tubes into the thermal block by imparting a uniform compressive load, and an insulator plate for insulating the thermal block assembly. As embodied herein and shown in FIGS. 1–5 and 26–30, second insulating cover 90 is provided on the top of the apparatus.

Second insulating cover includes a securing means 92 which will also be referred to as the top shell. Securing means 92 is a bracket with a top flange 94 and a side flange 96. The securing means 92 is preferably made out of 20% glass-filled polycarbonate, however, any other suitable insulation material is acceptable. The top flange 94 is located immediately above the second insulating plate, which will be described below. As shown in FIG. 1, a hinge 96 is provided so that the second insulating cover 90 and top resistive element heater 80 can be pivoted relative to the spacer bracket cover 49, spacer bracket 46, thermal block assembly 20, and first insulating cover 70. Hinge 96 includes a top hinge bracket 98 attached to the second insulating cover 90, and a bottom hinge bracket 100 attached to the spacer bracket cover 49.

Second insulating cover includes an insulation plate 110 as shown in FIGS. 1–5 and 28–30. Insulation plate 110 has a plurality of holes 112 corresponding to the sample wells. The holes allow radiation to be emitted into and out of the DNA sample as previously discussed. The insulation plate provides insulation for the top resistive element heater 80, first insulation cover 70, and thermal block assembly 20. The insulation plate 110 prevents heat loss through the top of the apparatus, thus promoting thermal block temperature uniformity. The insulation plate is preferably made out of 20% glass-filled polycarbonate, however, any other suitable insulation material is acceptable.

In accordance with the present invention, the apparatus further includes a radial fan to provide air to the heat sink. As embodied herein and shown in FIGS. 1-4, a radial fan 118 is provided adjacent the bottom fan duct 120. The bottom fan duct has a air inlet opening 122 through which ambient air enters the apparatus. The circulating air flows upward along the interior of the central fan duct 124. The circulating air then enters the spaces between the heat duct fins 32 and flow along the underside 35 of the heat sink 30. The heat sink transfers heat to the circulating air which then passes out of the apparatus through fan air exit plates 126. The fan air exit plates 126 are bolted onto flanges 128 of the central fan duct.

As previously discussed, the present invention is designed to increase the cycle life and reliability of the Peltier heaters. An additional way in which the reliability of the Peltier heaters is improved is by matching the thermal coefficient of expansion of the materials used for the structural components surrounding the Peltier heaters. Specifically, the copper thermal block plate, first insulating cover, spacer bracket and heat sink base plate have all been designed to have very similar thermal coefficients of expansion. During thermal cycling of a DNA sample, the Peltier heaters are structurally loaded with forces resulting from the expansion and contraction of these components. By providing similar thermal coefficients of expansion to these materials, the expansion and contraction forces on the Peltier heaters are minimized, thereby improving the cycle life of the solder joints within the Peltier heaters.

It will be understood that a suitable computer device, such as that includes a microprocessor, can be incorporated into the control electronics of the apparatus. The microprocessor controls the temperature of the apparatus and the amount of time that the apparatus is at each temperature in the thermal cycle. The microprocessor can be programmed to conduct the appropriate thermal cycle for each type of sample material.

The operation of the apparatus is described below. The second insulating cover 90 of the apparatus is opened up by pivoting about the hinges 96. A tray of disposable sample tubes are placed on top of the first insulating cover 70 so that the DNA in the sample tubes are positioned in the sample wells. The second insulating cover 90 is then closed.

Thermocycling can now be performed. The thermocycling is controlled by a controller. During thermocycling, the DNA will undergo a pre-programmed thermocycling process of raising and lowering temperatures in order to replicate the strands of DNA. Before undergoing the process, the temperature of the thermal block assembly is measured at at least one location. The controller then calculates the desired temperature of the thermal block assembly at the particular time. The desired temperature is then compared to the measured temperature. If the measured temperature is less than the desired temperature, heating of the thermal block assembly will occur. Heating the thermal block assembly comprises several steps. The first step is imparting a first heat rate via at least one first heater, a portion of the first heat rate being transferred to the thermal block assembly. The second step is imparting a second heat rate via a second heater, a portion of the second heat rate being transferred to the first heater. The third step is imparting a third heat rate via a third heater, a portion of the third heat rate being transferred to the top of the sample tubes in order to reduce the likelihood of condensation occurring on the top of sample tubes. It is understood that all three of these steps may be performed simultaneously.

Because a plurality of first heaters may be provided, the heat rate output of each of the plurality of first heaters may be independently controlled. This will allow the controller to monitor the sensor cup temperatures so that all of the sensor cups have a substantially equal temperature. Likewise, if a plurality of second heaters is provided, the heat rate output of each of the second heaters may also be independently controlled.

However, if the measured temperature is greater than the desired temperature, heating does not occur but instead the thermal block assembly will be cooled. This is done by reversing the current on the Peltier heaters in order to turn them into coolers, and by also imparting a cooling convection current on the heat sink which is thermally coupled to the thermal block assembly to provide heat transfer from the thermal block assembly to ambient air adjacent the heat sink. A radial fan may be provided for providing the convection current to the heat sink.

Once the step of heating or cooling is performed, the cycle continues by repeating the steps of measuring, calculating, and comparing until the predetermined thermal cycle for the samples of biological reaction mixture is completed. After the proper number of cycles have been performed, the top insulating cover will be opened and the DNA sample tubes will be removed from the sample wells.

The thermal cycling apparatus could also be modified to incorporate a temperature gradient means across the thermal block. A thermal cycling apparatus with a temperature gradient means is used to discover the optimum polymerase chain reaction annealing stage temperatures. The apparatus of the present invention is primarily focused towards producing the DNA via polymerase chain reactions once these temperatures are known. However, the apparatus for thermal cycling could be modified to include a temperature gradient means or independent temperature zones.

It will be apparent to those skilled in the art that various modifications and variations can be made in the apparatus and method for thermally cycling biological samples, use of the apparatus of the present invention, and in construction of this apparatus, without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for heating samples of biological material, comprising:

a thermal block assembly including a plurality of sample holders for receiving samples of biological material;

a heat sink thermally coupled to the thermal block assembly, said heat sink transferring heat away from the thermal block assembly to ambient air in contact with the heat sink;

a first heat source thermally coupled to the thermal block assembly to provide heat to the thermal block assembly, said first heat source generally positioned in a stacked relationship between the heat sink and the thermal block assembly; and a second heat source located below the first heat source with a substantial portion of the second heat source located outside the first heat source and thermally coupled to the first heat source to provide heat to at least a portion of the first heat source, wherein said thermal block assembly is positioned above the heat sink in said stacked relationship with the heat sink, and further wherein the arrangement of the heat sink, first heat source and second heat source provides substantial temperature uniformity among the plurality of sample holders.

2. The apparatus of claim 1, wherein said second heat source is located on an outer surface of the heat sink in order to cause a temperature gradient across the heat sink.

3. The apparatus of claim 2, wherein said first heat source includes at least one thermoelectric heater utilizing the Peltier effect, said first heat source producing a temperature gradient as a function of the temperature gradient across the heat sink, said temperature gradient of the first heat source causing the thermal block assembly to be urged toward said substantial temperature uniformity by heating at least a portion adjacent the edges of the thermal block assembly.

4. The apparatus of claim 3, wherein said second heat source is located adjacent at least a portion of the heat sink radially outside of the portion on which the first heat source is located.

5. The apparatus of claim 4, wherein said second heat source includes at least one resistive element heater.

6. The apparatus of claim 3, wherein during a first phase of operation, the first heat source and the second heat source work in conjunction to heat the thermal block assembly, and during a second phase of operation, the first heat source operates to direct heat away from the thermal block and into the heat sink.

7. The apparatus of claim 1, said first heat source including a first side and a second side, said first side having a higher temperature at an outer periphery of the first heat source than at an inner periphery of the first heat source corresponding approximately to a temperature gradient across the heat sink.

8. The apparatus of claim 1, wherein said thermal block assembly further comprises a thermal block plate.

9. The apparatus of claim 8, wherein said plurality of sample holders comprise a plurality of sample wells.

10. The apparatus of claim 9, wherein said plurality of sample wells are coupled to a surface of the thermal block plate.

11. The apparatus of claim 10, wherein said plurality of sample wells are attached to the thermal block plate by a method selected from a group consisting of silver brazing, copper casting, and ultrasonic welding.

12. The apparatus of claim 10, wherein said plurality of sample wells and thermal block plate are both composed of a copper alloy.

13. The apparatus of claim 1, wherein said first heat source includes at least one thermoelectric heater utilizing the Peltier effect, said at least one thermoelectric heater including a first side and second side, said first side typically being at a higher temperature than said second side during a heating of the sample, said apparatus further comprising a first thermal interface element located between the thermal block assembly and the first side of the at least one thermoelectric heater to provide heat transfer to the thermal block assembly.

14. The apparatus of claim 13, further comprising a second thermal interface element located between the heat sink and a lower temperature side of the at least one thermoelectric heater to provide heat transfer between the heat sink and the lower temperature side of the at least one thermoelectric heater and to improve the cycle life of the thermoelectric heater.

15. The apparatus of claim 1, wherein said thermal block assembly further comprises a thermal block plate, said plurality of sample holders being located on a surface of the thermal block plate, said apparatus further comprising:

a first cover of insulating material on the thermal block assembly; and a plurality of longitudinal fasteners for imparting a compressive force across said first cover, said thermal block plate, said first heat source, and said heat sink.

16. The apparatus of claim 15, wherein each said longitudinal fastener includes a screw and an insulating screw cap on one end of the longitudinal fastener, said insulating screw cap being located on a bottom surface of the heat sink.

17. The apparatus of claim 16, wherein each longitudinal fastener further includes an insulating washer located between the end of each longitudinal fastener and the bottom surface of the heat sink.

18. The apparatus of claim 1, further comprising a spacer bracket, each said first heat source being positioned in an opening in the spacer bracket.

19. The apparatus of claim 18, wherein said spacer bracket is sized so that the thermal block assembly is placed in compression.

20. The apparatus of claim 1, further comprising:

a first cover of insulating material, said first cover thermally insulating the sample holder of the thermal block assembly; and a third heat source, said third heat source including a plate located above the thermal block assembly to provide heat to a plurality of sample tubes respectively located in the sample wells of the thermal block assembly, wherein said sample holders comprise sample wells.

21. The apparatus of claim 20, further comprising:

a second cover of insulating material, said second cover thermally insulating the plurality of sample tubes respectively located in the sample wells of the thermal block assembly, said second cover comprising an assembly for holding the sample tubes in the thermal block by imparting a compressive load to improve the contact surface area between the respective heat sources and thermal block assembly, and a plate of insulating material for the thermal block assembly and first cover.

22. The apparatus of claim 21, wherein said holding assembly of the second cover includes a bracket with a clamping portion located adjacent the second cover for imparting said compressive load on the insulating plate.

23. The apparatus of claim 1, wherein said biological material includes a biological reaction mixture.

24. The apparatus of claim 23, wherein said apparatus is capable of thermally cycling said samples of biological reaction mixture.

25. The apparatus of claim 1, wherein the first heat source comprises at least one Peltier heater and the second heat source comprises at least one resistive heater.

26. The apparatus of claim 1 wherein the second heat source is located outside the first heat source.

27. An apparatus for heating samples of a biological material, comprising:

a thermal block assembly including a plurality of sample wells for receiving samples of biological material, each sample well having a length defined by the distance between a bottom surface of the sample well and a top edge surface of the sample well;

a first heat source thermally coupled to the thermal block assembly, said first heat source providing heat to the thermal block assembly;

a second heat source located below the first heat source with a substantial portion of the second heat source located outside the first heat source to provide heat to a portion of the first heat source; and a first cover of insulating material, said first cover thermally insulating the sample wells of the thermal block assembly, said first cover comprising a plate with a plurality of cylindrical sample well openings, each cylindrical sample well opening corresponding to a respective sample well, wherein the first cover includes a top portion configured to substantially cover the top edge surface of each of the sample wells, the first cover further including a peripheral portion configured to extend around a periphery of the plurality of sample wells and surround the plurality of sample wells along a substantial portion of the length of the sample wells.

28. The apparatus of claim 27, wherein each sample well extends for a substantial length of its respective cylindrical sample well opening in the first cover.

29. The apparatus of claim 27, wherein said thermal block assembly further comprises a thermal block plate, said plurality of sample wells being coupled to a surface of the thermal block plate.

30. The apparatus of claim 29, wherein the thermal block assembly further includes at least one sensor cup coupled to the surface of the thermal block plate, and wherein said first cover further includes at least one sensor cup opening corresponding to a respective sensor cup.

31. The apparatus of claim 27, further comprising:

a third heat source, said third heat source including a plate located above the thermal block assembly to provide heat to a plurality of sample tubes respectively located in a plurality of sample wells of the thermal block assembly.

32. The apparatus of claim 31, wherein said first heat source is a thermoelectric heater utilizing the Peltier effect, said second and third heat sources are resistive element heaters, and said samples of biological material is a biological reaction mixture including DNA.

33. The apparatus of claim 27, further comprising a heat sink thermally coupled to the thermal block assembly, wherein said second heat source is located on an outer surface of the heat sink in order to cause a temperature gradient on the heat sink.

34. The apparatus of claim 27, wherein the peripheral portion of the first cover is configured to surround the sample wells along the entire length of the sample wells.

35. The apparatus of claim 27 wherein the second heat source is located outside the first heat source.

36. An apparatus for thermally cycling samples of biological reaction mixture, comprising:

a thermal block assembly including a thermal block plate and a plurality of sample wells for receiving sample tubes containing biological reaction mixture;

a heat sink thermally coupled to the thermal block assembly, said heat sink transferring heat from the thermal block assembly to ambient air in contact with the heat sink, said thermal block assembly positioned above the heat sink in a stacked relationship with the heat sink;

at least one thermoelectric heater thermally coupled to the thermal block assembly, said at least one thermoelectric heater providing heat to the thermal block assembly, said at least one thermoelectric heater generally positioned in a stacked relationship between the heat sink and the thermal block assembly;

a thermal interface material between outer surfaces of the at least one thermoelectric heater and at least one of the thermal block assembly and heat sink, said thermal interface material providing heat transfer between the at least one thermoelectric heater and the at least one of the thermal block assembly and heat sink;

a first cover of insulating material for the sample wells of the thermal block assembly;

a first resistive element heater, said first resistive heater including a flat plate located above the thermal block assembly to provide heat to the thermal block assembly; and a second resistive element heater located below the at least one thermoelectric heater with a substantial portion of the second resistive element heater located outside the at least one thermoelectric heater for heating a bottom portion of said at least one thermoelectric heater.

37. The apparatus of claim 36, further comprising a second cover of insulating material including a holding assembly for holding the sample tubes in the sample wells by imparting a substantially uniform compressive load, and a plate of insulating material for the thermal block and first cover.

38. The apparatus of claim 36 wherein the second resistive element heater is located outside the at least one thermoelectric heater.

* * * * *